US012728089B2

(12) United States Patent
Blanc et al.

(10) Patent No.: US 12,728,089 B2
(45) Date of Patent: Sep. 8, 2026

(54) COMPOSITION COMPRISING TWO PARTICULAR OXIDATION DYE PRECURSORS AND A PARTICULAR AMINO SILICONE

(71) Applicant: L'OREAL, Paris (FR)

(72) Inventors: Julie Blanc, Saint-Ouen (FR); Laurence Cottard-Mei, Saint-Ouen (FR)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 18/717,318

(22) PCT Filed: Dec. 9, 2022

(86) PCT No.: PCT/EP2022/085109
§ 371 (c)(1),
(2) Date: Jun. 6, 2024

(87) PCT Pub. No.: WO2023/105022
PCT Pub. Date: Jun. 15, 2023

(65) Prior Publication Data

US 2025/0049694 A1 Feb. 13, 2025

(30) Foreign Application Priority Data

Dec. 10, 2021 (FR) ...................................... 2113300

(51) Int. Cl.
*A61Q 5/10* (2006.01)
*A61K 8/894* (2006.01)

(52) U.S. Cl.
CPC ................ *A61K 8/894* (2013.01); *A61Q 5/10* (2013.01); *A61K 2800/43* (2013.01); *A61K 2800/54* (2013.01); *A61K 2800/591* (2013.01); *A61K 2800/882* (2013.01)

(58) Field of Classification Search
CPC ................ A61K 8/894; A61K 2800/43; A61K 2800/54; A61K 2800/591; A61K 2800/882; A61K 8/49; A61K 8/585; A61K 8/89; A61Q 5/10
USPC ..................................................... 8/405, 406
See application file for complete search history.

(56) References Cited

U.S. PATENT DOCUMENTS 2,261,002 A 10/1941 Moore
2,271,387 A 1/1942 Charles
2,273,780 A 2/1942 Dittmar
2,375,853 A 5/1945 Kirby et al.
2,388,614 A 11/1945 Kirby et al.
2,454,547 A 11/1948 Bock et al.
2,961,347 A 11/1960 Floyd
3,206,462 A 9/1965 Mccarty
3,227,615 A 1/1966 Korden
3,472,840 A 10/1969 Stone et al.
3,589,578 A 6/1971 Kamal et al.
3,632,559 A 1/1972 Matter et al.
3,874,870 A 4/1975 Green et al.
3,910,862 A 10/1975 Barabas et al.
3,912,808 A 10/1975 Sokol
3,917,817 A 11/1975 Vanlerberghe et al.
3,929,990 A 12/1975 Green et al.
3,966,904 A 6/1976 Green et al.
4,001,432 A 1/1977 Green et al.
4,005,193 A 1/1977 Green et al.
4,025,617 A 5/1977 Green et al.
4,025,627 A 5/1977 Green et al.
4,025,653 A 5/1977 Green et al.
4,026,945 A 5/1977 Green et al.
4,027,020 A 5/1977 Green et al.
4,031,307 A 6/1977 Demartino et al.
4,075,136 A 2/1978 Schaper
4,131,576 A 12/1978 Iovine
4,137,180 A 1/1979 Naik et al.
4,157,388 A 6/1979 Christiansen
4,165,367 A 8/1979 Chakrabarti
4,172,887 A 10/1979 Grollier et al.
RE30,199 E 1/1980 Rose
4,217,914 A 8/1980 Jacquet
4,240,450 A 12/1980 Grollier
(Continued)

FOREIGN PATENT DOCUMENTS

DE 202009011154 U1 10/2009
EP 0080976 A1 6/1983
(Continued)

OTHER PUBLICATIONS

International Preliminary Report on Patentability in PCT/EP2022/085104, mailed Jun. 20, 2024, 7 pages.
International Preliminary Report on Patentability in PCT/EP2022/085109, mailed Jun. 20, 2024, 7 pages.
International Search Report and Written Opinion in PCT/EP2022/085104, mailed Mar. 9, 2023, 10 pages.
International Search Report and Written Opinion in PCT/EP2022/085109, mailed Mar. 9, 2023, 10 pages.
Porter, M.R., "Handbook of Surfactants," published by Blackie & Son Glasgow and London, 1991, pp. 116-178.
U.S. Appl. No. 18/717,326, filed Jun. 6, 2024, 56 pages.

*Primary Examiner* — Eisa B Elhilo
(74) *Attorney, Agent, or Firm* — The Marbury Law Group, PLLC.

(57) ABSTRACT

The invention relates to a composition comprising at least one oxidation dyeing base chosen from the derivatives of para-phenylenediamine of formula (I), addition salts thereof, solvates thereof and/or solvates of the salts thereof, at least one oxidation coupler chosen from 6-hydroxybenzomorpholine of formula (II), an addition salt thereof, solvates thereof and/or solvates of the salts thereof, and at least one (poly) oxyalkylenated amino silicone.

The invention also relates to a process for dyeing keratin fibers, preferably the hair, which comprises the application of the composition to said keratin fibers.

18 Claims, No Drawings

(56) References Cited

U.S. PATENT DOCUMENTS

| | | | |
|---|---|---|---|
| 4,349,532 | A | 9/1982 | Vanlerberghe et al. |
| 4,381,919 | A | 5/1983 | Jacquet et al. |
| 4,591,610 | A | 5/1986 | Grollier |
| 4,702,906 | A | 10/1987 | Jacquet et al. |
| 4,719,282 | A | 1/1988 | Nadolsky et al. |
| 4,761,273 | A | 8/1988 | Grollier et al. |
| 4,823,985 | A | 4/1989 | Grollier et al. |
| 4,839,166 | A | 6/1989 | Grollier et al. |
| 4,874,554 | A | 10/1989 | Lange et al. |
| 4,996,059 | A | 2/1991 | Grollier et al. |
| 5,061,289 | A | 10/1991 | Clausen et al. |
| 5,089,252 | A | 2/1992 | Grollier et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,766,576 | A | 6/1998 | Lowe et al. |
| 6,099,592 | A | 8/2000 | Mdal et al. |
| 6,099,593 | A | 8/2000 | Terranova et al. |
| 6,284,003 | B1 | 9/2001 | Rose et al. |
| 6,730,789 | B1 | 5/2004 | Birault et al. |
| 9,474,700 | B2 | 10/2016 | Salvemini et al. |
| 10,555,891 | B2 * | 2/2020 | Patterson ............... A61K 8/585 |
| 2005/0188477 | A1 | 9/2005 | Plos |
| 2007/0226917 | A1 * | 10/2007 | Kleen ...................... A61Q 5/10 8/406 |
| 2020/0261338 | A1 * | 8/2020 | Ronchard ................ A61Q 5/06 |

FOREIGN PATENT DOCUMENTS

| | | | |
|---|---|---|---|
| EP | 0122324 | A1 | 10/1984 |
| EP | 0337354 | A1 | 10/1989 |
| EP | 0770375 | A1 | 5/1997 |
| FR | 2886136 | A1 | 12/2006 |
| GB | 1026978 | A | 4/1966 |
| GB | 1153196 | A | 5/1969 |
| GB | 1546809 | A | 5/1979 |
| JP | H0219576 | A | 1/1990 |
| JP | H0563124 | A | 3/1993 |
| WO | 2023105019 | A1 | 6/2023 |

* cited by examiner

COMPOSITION COMPRISING TWO PARTICULAR OXIDATION DYE PRECURSORS AND A PARTICULAR AMINO SILICONE

CROSS REFERENCE TO RELATED APPLICATIONS

This is a National Stage Application of PCT/EP2022/085109, filed internationally on Dec. 9, 2022, which claims priority to French Application No. 2113300, filed on Dec. 10, 2021, which are incorporated by reference herein in their entireties.

The invention relates to a composition comprising the combination of a particular oxidation base, of a particular oxidation coupler and of a (poly)oxyalkylenated amino silicone, notably for dyeing keratin fibers.

The invention also relates to a process for dyeing keratin fibers, notably the hair, using this composition.

Finally, the invention relates to the use of such a composition for dyeing keratin fibers, and notably the hair.

Many people have sought for a long time to modify the color of their hair and in particular to mask their gray hair.

It is known practice to dye keratin fibers, in particular human keratin fibers such as the hair, to obtain "permanent" colorings with dyeing compositions containing oxidation dye precursors, notably oxidation bases, such as ortho- or para-phenylenediamines, ortho- or para-aminophenols, or heterocyclic compounds such as pyrazoles, pyrazolinones or pyrazolopyridines. These oxidation bases are colorless or weakly colored compounds which, when combined with oxidizing products, can give rise to colored compounds via a process of oxidative condensation.

It is also possible to vary the shades obtained with these oxidation bases by combining them with couplers or color modifiers. The variety of molecules used as oxidation bases and couplers allows a wide range of colors to be obtained. However, the use of these dye compositions may have a certain number of drawbacks.

Specifically, after application to keratin fibers, the dyeing power obtained may not be entirely satisfactory, or may even be weak, and lead to a restricted range of colors.

The colorings may also be insufficiently persistent with respect to external agents such as light, shampoo or perspiration, and may also be too selective, i.e. the difference in coloring is too great along the same keratin fiber that is differently sensitized between its end and its root.

There is a real need for a composition for dyeing keratin fibers, in particular human keratin fibers such as the hair, which does not have the abovementioned drawbacks, i.e. which is capable of leading to a coloring with an intense color with improved persistence and also good coverage of gray hair and good selectivity, and which is capable of giving good dyeing performance, even after a period of storage.

These aims and others are achieved by the present invention, one subject of which is thus a composition, preferably a cosmetic composition, notably for dyeing keratin fibers, comprising:

at least one oxidation base chosen from the derivatives of para-phenylenediamine of formula (I), addition salts thereof, solvates thereof and/or solvates of the salts thereof:

(I)

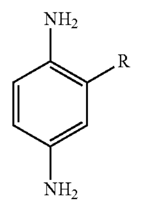

in which R is chosen from:

i) a $(C_1-C_4)$alkoxy$(C_1-C_4)$alkyl radical, ii) a $C_1-C_4$ hydroxyalkyl radical;

at least one oxidation coupler chosen from 6-hydroxybenzomorpholine of formula (II), an addition salt thereof, solvates thereof and/or solvates of the salts thereof and mixtures thereof:

(II)

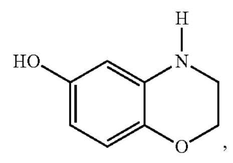

and at least one (poly)oxyalkylenated amino silicone.

The present invention also relates to a process for dyeing keratin fibers in which the composition according to the invention is applied to said fibers.

According to a preferred embodiment, the composition according to the invention is a composition for dyeing keratin fibers, notably the hair.

The composition according to the invention may notably lead to chromatic, powerful, intense and sparingly selective colorings, i.e. colorings that are uniform along the length of the fiber. It also allows various shades to be achieved in a very wide range of colors. It also enables good color build-up.

This composition also gives particularly good coverage of depigmented keratin fibers such as gray hair.

A subject of the invention is also a kit comprising, in a first compartment, a composition as defined previously and, in a second compartment, an oxidizing composition comprising at least one chemical oxidizing agent.

According to the invention, the term "chemical oxidizing agent" means an oxidizing agent other than atmospheric oxygen.

Other subjects, features, aspects and advantages of the invention will emerge even more clearly on reading the description and the examples that follow.

In the text hereinbelow, unless otherwise indicated, the limits of a range of values are included in that range, notably in the expressions "between" and "ranging from . . . to . . . ".

Moreover, the expression "at least one" used in the present description is equivalent to the expression "one or more".

The composition according to the invention comprises at least one particular oxidation base.

Oxidation Bases

The composition according to the invention comprises at least one oxidation base chosen from the derivatives of para-phenylenediamine of formula (I), addition salts thereof, solvates thereof and/or solvates of the salts thereof:

(I)

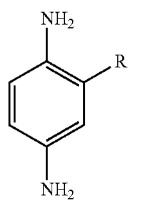

in which R is chosen from:

i) a $(C_1-C_4)$alkoxy$(C_1-C_4)$alkyl radical, ii) a $C_1-C_4$ hydroxyalkyl radical.

The term "alkyl" radical is intended to mean a saturated, linear or branched, hydrocarbon-based chain.

The term $(C_1-C_4)$alkoxy$(C_1-C_4)$alkyl radical is intended to mean an alkyl-O-alkyl radical, each of the alkyl groups, independently of one another, comprising 1 to 4 carbon atoms.

The term $C_1-C_4$ hydroxyalkyl radical is intended to mean an alkyl radical substituted by a hydroxy (alkyl-OH) group, the alkyl radical comprising from 1 to 4 carbon atoms.

Preferably, the derivative(s) of para-phenylenediamine of formula (I) is(are) chosen from those in which R is chosen from:

i) a $(C_1-C_2)$alkoxy$(C_1-C_2)$alkyl radical, preferably a methoxymethyl radical;

ii) a $C_1-C_3$, preferably $C_2-C_3$, hydroxyalkyl radical, more preferentially $CH_2CH_2OH$, $CH_2CH_2CH_2OH$ radical.

The addition salts of the compound of formula (I), which may be present in the composition according to the invention, are notably chosen from the addition salts with an acid, such as the hydrochlorides, hydrobromides, sulfates, citrates, succinates, tartrates, lactates, tosylates, benzenesulfonates, phosphates and acetates, and the addition salts with a base such as sodium hydroxide, potassium hydroxide, aqueous ammonia, amines or alkanolamines.

Moreover, the solvates of the compound of formula (I) more particularly represent the hydrates of said compound and/or the combination of said compound with a linear or branched C1 to C4 alcohol such as methanol, ethanol, isopropanol or n-propanol. Preferably, the solvates are hydrates.

Preferably, the oxidation base(s) chosen from the derivatives of para-phenylenediamine of formula (I), addition salts thereof, solvates thereof and/or solvates of the salts thereof is(are) chosen from 2-methoxymethyl-para-phenylenediamine, 2-β-hydroxyethyl-para-phenylenediamine, 2-γ-hydroxypropyl-para-phenylenediamine, an addition salt thereof, solvates thereof and/or solvates of the salts thereof.

Preferably, the total content of the oxidation base(s) chosen from the derivatives of para-phenylenediamine of formula (I), an addition salt thereof, solvates thereof and/or solvates of the salts thereof ranges from 0.001% to 20% by weight, preferably from 0.005% to 15% by weight, more preferentially from 0.01% to 10% by weight, better still from 0.05% to 5% by weight, and even better still from 0.1% to 3% by weight, relative to the weight of the composition.

When it is present, the total content of the oxidation base chosen from 2-methoxymethyl-para-phenylenediamine, an addition salt thereof, solvates thereof and/or solvates of the salts thereof preferably ranges from 0.001% to 20% by weight, more preferably from 0.005% to 15% by weight, more preferentially from 0.01% to 10% by weight, better still from 0.05% to 5% by weight, and even better still from 0.1% to 3% by weight, relative to the weight of the composition.

When it is present, the total content of the oxidation base chosen from 2-β-hydroxyethyl-para-phenylenediamine, an addition salt thereof, solvates thereof and/or solvates of the salts thereof preferably ranges from 0.001% to 20% by weight, more preferably from 0.005% to 15% by weight, more preferentially from 0.01% to 10% by weight, better still from 0.05% to 5% by weight, and even better still from 0.1% to 3% by weight, relative to the weight of the composition.

When it is present, the total content of the oxidation base chosen from 2-γ-hydroxypropyl-para-phenylenediamine, an addition salt thereof, solvates thereof and/or solvates of the salts thereof preferably ranges from 0.001% to 20% by weight, more preferably from 0.005% to 15% by weight, more preferentially from 0.01% to 10% by weight, better still from 0.05% to 5% by weight, and even better still from 0.1% to 3% by weight, relative to the weight of the composition.

The composition according to the invention may optionally also comprise one or more additional oxidation base(s) other than the compound of formula (I), addition salts thereof, solvates thereof and/or solvates of the salts thereof, chosen from para-phenylenediamines, bis(phenyl)alkylenediamines, para-aminophenols, ortho-aminophenols and heterocyclic bases, addition salts thereof, solvates and solvates of the salts thereof.

Among the para-phenylenediamines, other than the compound of formula (I), examples that may be mentioned include para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, 4-N,N-bis(β-hydroxyethyl)amino-2-methylaniline, 4-N,N-bis(β-hydroxyethyl)amino-2-chloroaniline, 2-fluoro-para-phenylenediamine, 2-isopropyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, addition salts thereof, solvates and solvates of the salts thereof.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, addition salts thereof, solvates thereof and solvates of the salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(3-hydroxyethylaminomethyl)phenol and 4-amino-2-fluorophenol, addition salts thereof, solvates thereof, solvates of the salts thereof.

Among the ortho-aminophenols, examples that may be mentioned include 2-aminophenol, 2-amino-5-methylphenol, 2-amino-6-methylphenol and 5-acetamido-2-aminophenol, addition salts thereof, solvates thereof, solvates of the salts thereof.

Among the heterocyclic bases, examples that may be mentioned include pyridine derivatives, pyrimidine derivatives and pyrazole derivatives.

Among the pyridine derivatives that may be mentioned are the compounds for example described in patents GB 1 026 978 and GB 1 153 196, for example 2,5-diaminopyridine, 2-(4-methoxyphenyl)amino-3-aminopyridine and 3,4-diaminopyridine and corresponding addition salts, solvates and solvates of the salts thereof.

Other pyridine oxidation bases which are useful in the present invention are the oxidation bases of 3-aminopyrazolo[1,5-a]pyridine or corresponding addition salts described, for example, in patent application FR 2 801308. Examples which may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo[1,5-a]pyridine, and corresponding addition salts, solvates and/or solvates of the salts thereof.

More particularly, the oxidation bases that are useful in the present invention are chosen from 3-aminopyrazolo[1,5-a]pyridines and are preferably substituted on carbon atom 2 with:

a) a (di)($C_1$-$C_6$)(alkyl)amino group, said alkyl group possibly being substituted with at least one hydroxyl, amino or imidazolium group;
b) an optionally cationic 5- to 7-membered heterocycloalkyl group comprising from 1 to 3 heteroatoms, optionally substituted with one or more ($C_1$-$C_6$)alkyl groups such as a di($C_1$-$C_4$)alkylpiperazinium group; or
c) a ($C_1$-$C_6$)alkoxy group optionally substituted with one or more hydroxyl groups, such as a β-hydroxyalkoxy group, and corresponding addition salts, solvates and/or solvates of the salts thereof.

Among the pyrimidine derivatives that may be mentioned are the compounds described, for example, in patents DE 2 359 399; JP 88-169 571; JP 05-63124; EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and addition salts thereof, solvates thereof, solvates of the salts thereof and tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, such as 4,5-diamino-1-methylpyrazole, 4,5-diamino-1-((3-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-((3-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-((3-hydroxyethyl)amino-1-methylpyrazole, and corresponding addition salts, solvates and solvates of the salts thereof. Use may also be made of 4,5-diamino-1-((3-methoxyethyl)pyrazole.

A 4,5-diaminopyrazole will preferably be used and even more preferentially 4,5-diamino-1-(β-hydroxyethyl)pyrazole and/or a corresponding salt, solvates and solvates of the salts thereof.

The pyrazole derivatives that may also be mentioned include diamino-N,N-dihydropyrazolopyrazolones and in particular those described in patent application FR-A-2 886 136, such as the following compounds and the corresponding addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a corresponding salt, solvates and solvates of the salts thereof.

Heterocyclic bases that will preferably be used include 4,5-diamino-1-(β-hydroxyethyl)pyrazole and/or 2,3-diamino-6,7-dihydro-1H,5H-pyrazolo[1,2-a]pyrazol-1-one and/or 2-β-hydroxyethoxy-3-amino-pyrazolo[1,5-a]pyridine and/or a corresponding salt.

These compounds may also be present in the form of solvates.

The addition salts of the additional oxidation bases that may be present in the composition according to the invention are notably chosen from the addition salts with an acid, such as the hydrochlorides, hydrobromides, sulfates, citrates, succinates, tartrates, lactates, tosylates, benzenesulfonates, methanesulfonates, phosphates and acetates, and the addition salts with a base such as sodium hydroxide, potassium hydroxide, aqueous ammonia, amines or alkanolamines.

Moreover, the solvates of the additional oxidation bases more particularly represent the hydrates of said oxidation bases and/or the combination of said oxidation bases with a linear or branched $C_1$ to $C_4$ alcohol such as methanol, ethanol, isopropanol or n-propanol. Preferably, the solvates are hydrates.

In a particular embodiment, the composition according to the invention is free of oxidation bases chosen from para-phenylenediamine, para-toluenediamine, addition salts thereof, solvates thereof and solvates of the salts thereof.

When the composition according to the invention comprises one or more additional oxidation base(s), the total content of the additional oxidation base(s), other than the derivatives of para-phenylenediamines of formula (I), addition salts thereof, solvates thereof and solvates of the salts thereof, present in the composition according to the invention, preferably ranges from 0.001% to 20% by weight, more preferably from 0.005% to 15% by weight, more preferentially from 0.01% to 10% by weight, better still from 0.05% to 5%, even better still from 0.1% to 3% by weight, relative to the total weight of the composition.

The composition according to the invention comprises at least one particular oxidation coupler.

Oxidation Couplers

The composition according to the present invention comprises at least one coupler chosen from 6-hydroxybenzomorpholine of formula (II), an addition salt thereof, solvates thereof and/or solvates of the salts thereof and mixtures thereof:

(II)

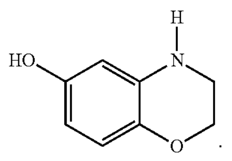

The addition salts of the compounds of formula (II) are notably chosen from the addition salts with an acid, such as the hydrochlorides, hydrobromides, sulfates, citrates, succinates, tartrates, lactates, tosylates, benzenesulfonates, phosphates and acetates, and the addition salts with a base such as sodium hydroxide, potassium hydroxide, aqueous ammonia, amines or alkanolamines.

Moreover, the solvates of the compounds of formula (II) more particularly represent the hydrates of these compounds and/or the combination of these compounds with a linear or branched $C_1$ to $C_4$ alcohol such as methanol, ethanol, isopropanol or n-propanol. Preferably, the solvates are hydrates.

Preferably, the total content of coupler(s) chosen from 6-hydroxybenzomorpholine of formula (II), an addition salt thereof, solvates thereof and/or solvates of the salts thereof ranges from 0.001% to 20% by weight, preferably from 0.005% to 15% by weight, more preferentially from 0.01% to 10% by weight, better still from 0.05% to 5%, even better still from 0.1% to 3% by weight, relative to the total weight of the composition.

The composition according to the invention may optionally also comprise one or more additional coupler(s), other than the compound of formula (II), and addition salts thereof, solvates thereof and/or the solvates of the salts thereof, advantageously chosen from those conventionally used in the dyeing of keratin fibers.

Among the additional couplers, mention may be made in particular of meta-phenylenediamines, meta-aminophenols, meta-diphenols, naphthalene-based coupling agents and heterocyclic coupling agents, and also the corresponding addition salts, the solvates and the solvates of the salts thereof.

Mention may be made, for example, of 2-amino-5-ethylphenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, α-naphthol, 2-methyl-1-naphthol, 6-hydroxyindole, 4-hydroxyindole, 4-hydroxy-N-methylindole, 2-amino-3-hydroxypyridine, 3,5-diamino-2,6-dimethoxypyridine, 2,6-bis(pi-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b][1,2,4]triazole, 2,6-dimethyl[3,2-c][1,2,4]triazole and 6-methylpyrazolo[1,5-a]benzimidazole, 2-methyl-5-aminophenol, 5-N-(β-hydroxyethyl)amino-2-methylphenol, 3-aminophenol, 3-amino-2-chloro-6-methylphenol and hydroxyethyl-3,4-methylenedioxyaniline, the addition salts, the solvates, the solvates of the salts thereof, and the corresponding mixtures.

In a particular embodiment, the composition according to the invention is free of oxidation couplers chosen from resorcinol, 2-methylresorcinol, 4-chlororesorcinol, addition salts thereof, solvates thereof and the solvates of the salts thereof.

In general, the addition salts of the couplers that may be used in the context of the invention are chosen in particular from the addition salts with an acid such as the hydrochlorides, hydrobromides, sulfates, citrates, succinates, tartrates, lactates, tosylates, benzenesulfonates, phosphates and acetates and the addition salts with a base such as sodium hydroxide, potassium hydroxide, aqueous ammonia, amines or alkanolamines.

When the composition comprises one or more additional oxidation coupler(s), the total content of the additional coupler(s), other than the couplers of formula (II), salts thereof, solvates thereof and solvates of the salts thereof, present in the composition according to the invention, preferably ranges from 0.001% to 20% by weight, more preferably from 0.005% to 15% by weight, more preferentially from 0.01% to 10% by weight, better still from 0.05% to 5% by weight and even better still from 0.1% to 3% by weight, relative to the total weight of the composition.

Advantageously, the weight ratio between the total content of oxidation base(s) chosen from the derivatives of para-phenylenediamine of formula (I), an addition salt thereof, solvates thereof and solvates of the salts thereof and the total content of oxidation coupler(s) chosen from 6-hydroxybenzomorpholine of formula (II), an addition salt thereof, solvates thereof and/or solvates of the salts thereof is between 0.1 and 10, preferably between 0.5 and 5.

Advantageously, the weight ratio between the total content of the oxidation base(s) and the total content of the coupler(s) is between 0.1 and 10, preferably between 0.3 and 3.

(Poly)Oxyalkylenated Amino Silicone

The composition according to the invention also comprises one or more (poly)oxyalkylenated amino silicone(s).

The (poly)oxyalkylenated amino silicones that are useful according to the invention are silicones comprising at least one primary, secondary or tertiary amine group or a quaternary ammonium group, and at least one oxyalkylenated group of the ($—CnH_2nO—$) type in which n may range from 2 to 6, and preferably n is equal to 2 or 3.

According to a particular embodiment, the (poly)oxyalkylenated amino silicones that are useful according to the invention are multiblock (poly)oxyalkylenated amino silicones of (AB)m type, A being a polysiloxane block and B being a (poly)oxyalkylene block, comprising at least one amine group.

Said silicones are preferably formed from repeating units having the following general formulae:

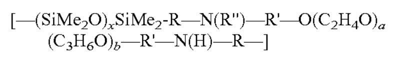

$[—(SiMe_2O)_xSiMe_2\text{-}R—N(R'')—R'—O(C_2H_4O)_a(C_3H_6O)_b—R'—N(H)—R—]$ or alternatively

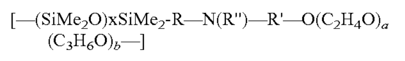

$[—(SiMe_2O)xSiMe_2\text{-}R—N(R'')—R'—O(C_2H_4O)_a(C_3H_6O)_b—]$ in which:

- a is an integer greater than or equal to 1, preferably ranging from 5 to 200 and more particularly ranging from 10 to 100;
- b is an integer between 0 and 200, preferably ranging from 4 to 100 and more particularly between 5 and 30;
- x is an integer ranging from 1 to 10 000 and more particularly from 10 to 5000;
- R" is a hydrogen atom or a methyl;
- R, which may be identical or different, represent a linear or branched divalent $C_2$-$C_{12}$ hydrocarbon-based radical, optionally including one or more heteroatoms such as oxygen; preferably, R denotes an ethylene radical, a linear or branched propylene radical, a linear or branched butylene radical or a $CH_2CH_2CH_2OCH_2CH(OH)CH_2—$ radical; preferentially, R denotes a $CH_2CH_2CH_2OCH_2CH(OH)CH_2—$ radical;
- R', which may be identical or different, represent a linear or branched divalent $C_2$-$C_{12}$ hydrocarbon-based radical, optionally including one or more heteroatoms such as oxygen; preferably, R' denotes an ethylene radical, a linear or branched propylene radical, a linear or branched butylene radical or a radical $CH_2CH_2CH_2OCH_2CH(OH)CH_2—$; preferentially, R' denotes $—CH(CH_3)—CH_2—$.

The siloxane blocks preferably represent between 50 mol % and 95 mol % of the total weight of the silicone, more particularly from 70 mol % to 85 mol %.

The amine content is preferably between 0.02 and 0.5 meq/g of copolymer in a 30% solution in dipropylene glycol, more particularly between 0.05 and 0.2.

The weight-average molecular mass (Mw) of the silicone is preferably between 5000 and 1 000 000 and more particularly between 10 000 and 200 000.

Mention may notably be made of the silicones sold under the name Silsoft A-843 or Silsoft A+ by Momentive.

Preferably, a (poly)oxyalkylenated amino silicone having the INCI name PEG-40/PPG-8 methylaminopropyl/hydroxypropyl dimethicone copolymer is used.

Preferably, the (poly)oxyalkylenated amino silicone(s) is/are generally present in a total content ranging from 0.01% to 10% by weight, preferably from 0.05% to 5% by weight, more preferentially from 0.075% to 4% by weight and better still from 0.1% to 2% by weight relative to the total weight of the composition.

Fatty Substance

The composition according to the invention may comprise one or more fatty substances other than the (poly)oxyalkylenated amino silicones.

The term "fatty substance" means an organic compound that is insoluble in water at 25° C. and at atmospheric pressure ($1.013\times10^5$ Pa) (solubility of less than 5% by weight, preferably less than 1% by weight, even more preferentially less than 0.1% by weight). They bear in their structure at least one hydrocarbon-based chain including at least 6 carbon atoms and/or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

Advantageously, the fatty substances that may be used in the present invention are neither (poly)oxyalkylenated nor (poly)glycerolated.

Preferably, the fatty substances that are useful according to the invention are nonsilicone fatty substances.

The term "nonsilicone fatty substance" refers to a fatty substance not containing any Si—O bonds and the term "silicone fatty substance" refers to a fatty substance containing at least one Si—O bond.

The fatty substances that are useful according to the invention may be liquid fatty substances (or oils) and/or solid fatty substances. The term "liquid fatty substance" means a fatty substance having a melting point of less than or equal to 25° C. at atmospheric pressure ($1.013\times10^5$ Pa). The term "solid fatty substance" means a fatty substance having a melting point of greater than 25° C. at atmospheric pressure ($1.013\times10^5$ Pa).

For the purposes of the present invention, the melting point corresponds to the temperature of the most endothermic peak observed on thermal analysis (differential scanning calorimetry or DSC) as described in the standard ISO 11357-3; 1999. The melting point may be measured using a differential scanning calorimeter (DSC), for example the calorimeter sold under the name MDSC 2920 by the company TA Instruments. In the present patent application, all the melting points are determined at atmospheric pressure ($1.013\times10^5$ Pa).

More particularly, the liquid fatty substance(s) according to the invention are chosen from C6 to C16 liquid hydrocarbons, liquid hydrocarbons comprising more than 16 carbon atoms, nonsilicone oils of animal origin, oils of triglyceride type of plant or synthetic origin, fluoro oils, liquid fatty alcohols, liquid fatty acid and/or fatty alcohol esters other than triglycerides, and mixtures thereof.

It is recalled that the fatty alcohols, esters and acids more particularly contain at least one saturated or unsaturated, linear or branched hydrocarbon-based group comprising from 6 to 40 and better still from 8 to 30 carbon atoms, which is optionally substituted, in particular with one or more hydroxyl groups (in particular 1 to 4). If they are unsaturated, these compounds may comprise one to three conjugated or unconjugated carbon-carbon double bonds.

As regards the C6 to C16 liquid hydrocarbons, they may be linear, branched, or optionally cyclic, and are preferably chosen from alkanes. Examples that may be mentioned include hexane, cyclohexane, undecane, dodecane, isododecane, tridecane or isoparaffins, such as isohexadecane or isodecane, and mixtures thereof.

The liquid hydrocarbons comprising more than 16 carbon atoms may be linear or branched, and of mineral or synthetic origin, and are preferably chosen from liquid paraffins or liquid petroleum jelly (INCI name: mineral oil or paraffinum liquidum), polydecenes, hydrogenated polyisobutene such as Parleam®, and mixtures thereof.

A hydrocarbon-based oil of animal origin that may be mentioned is perhydrosqualene.

The triglyceride oils of plant or synthetic origin are preferably chosen from liquid fatty acid triglycerides including from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stearinerie Dubois or those sold under the names Miglyol® 810, 812 and 818 by the company Dynamit Nobel, jojoba oil and shea butter oil, and mixtures thereof.

As regards the fluoro oils, they may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethylperfluoromorpholine sold under the name PF 5052® by the company 3M.

The liquid fatty alcohols that are suitable for use in the invention are more particularly chosen from linear or branched, saturated or unsaturated alcohols, preferably unsaturated or branched alcohols, including from 6 to 40 carbon atoms and preferably from 8 to 30 carbon atoms. Examples that may be mentioned include octyldodecanol, 2-butyloctanol, 2-hexyldecanol, 2-undecylpentadecanol, isostearyl alcohol, oleyl alcohol, linolenyl alcohol, ricinoleyl alcohol, undecylenyl alcohol and linoleyl alcohol, and mixtures thereof.

As regards the liquid esters of fatty acids and/or of fatty alcohols, other than the triglycerides mentioned previously, mention may be made notably of esters of saturated or unsaturated, linear C1 to C26 or branched C3 to C26 aliphatic mono- or polyacids and of saturated or unsaturated, linear C1 to C26 or branched C3 to C26 aliphatic mono- or polyalcohols, the total carbon number of the esters being greater than or equal to 6 and more advantageously greater than or equal to 10.

Preferably, for the esters of monoalcohols, at least one from among the alcohol and the acid from which the esters of the invention are derived is branched.

Among the monoesters, mention may be made of dihydroabietyl behenate; octyldodecyl behenate; isocetyl behenate; isostearyl lactate; lauryl lactate; linoleyl lactate; oleyl lactate; isostearyl octanoate; isocetyl octanoate; octyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; octyl isononanoate; 2-ethylhexyl isononanoate; octyldodecyl erucate; oleyl erucate; ethyl palmitate, isopropyl palmitate, 2-ethylhexyl palmitate, 2-octyldecyl palmitate, alkyl myristates such as isopropyl myristate, isobutyl stearate; 2-hexyldecyl laurate, and mixtures thereof.

Preferably, among the monoesters of monoacids and of monoalcohols, use will be made of ethyl palmitate and isopropyl palmitate, alkyl myristates such as isopropyl myristate or ethyl myristate, isocetyl stearate, 2-ethylhexyl isononanoate, isodecyl neopentanoate and isostearyl neopentanoate, and mixtures thereof. Still within the context of this variant, esters of C4-C22 dicarboxylic or tricarboxylic acids and of C1-C22 alcohols and esters of monocarboxylic, dicarboxylic or tricarboxylic acids and of C2-C26 dihydroxy, trihydroxy, tetrahydroxy or pentahydroxy alcohols may also be used.

Mention may notably be made of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

The composition may also comprise, as fatty ester, sugar esters and diesters of C6 to C30 and preferably C12 to C22 fatty acids. It is recalled that the term "sugar" refers to oxygen-bearing hydrocarbon-based compounds bearing several alcohol functions, with or without aldehyde or ketone functions, and which include at least 4 carbon atoms. These sugars may be monosaccharides, oligosaccharides or polysaccharides.

Examples of suitable sugars that may be mentioned include sucrose, glucose, galactose, ribose, fucose, maltose, fructose, mannose, arabinose, xylose and lactose, and derivatives thereof, notably alkyl derivatives, such as methyl derivatives, for instance methylglucose.

The sugar esters of fatty acids may be chosen notably from the group comprising the esters or mixtures of esters of sugars described above and of linear or branched, saturated or unsaturated C6 to C30 and preferably C12 to C22 fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates, arachidonates or mixtures thereof notably such as the mixed oleo-palmitate, oleo-stearate and palmito-stearate esters.

More particularly, use is made of monoesters and diesters and notably sucrose, glucose or methylglucose mono- or di-oleates, -stearates, -behenates, -oleopalmitates, -linoleates, -linolenates and -oleostearates, and mixtures thereof.

An example that may be mentioned is the product sold under the name Glucate® DO by the company Amerchol, which is a methylglucose dioleate.

Preferably, use will be made of a liquid ester of a monoacid and of a monoalcohol, more preferentially isopropyl myristate.

The solid fatty substances according to the invention preferably have a viscosity of greater than 2 Pa·s, measured at 25° C. and at a shear rate of 1 s-.

The solid fatty substance(s) are preferably chosen from solid fatty acids, solid fatty alcohols, solid esters of fatty acids and/or of fatty alcohols, waxes, ceramides and mixtures thereof.

The term "fatty acid" means a long-chain carboxylic acid comprising from 6 to 40 carbon atoms, preferably from 8 to 30 carbon atoms. The solid fatty acids according to the invention preferentially comprise from 10 to 30 carbon atoms, better still from 12 to 24 carbon atoms, and even better still from 14 to 22 carbon atoms. They may optionally be hydroxylated. These fatty acids are neither oxyalkylenated nor glycerolated.

The solid fatty acids that may be used in the present invention are notably chosen from myristic acid, cetylic acid (also called palmitic acid), arachidic acid, stearic acid, lauric acid, behenic acid, 12-hydroxystearic acid, and mixtures thereof.

Particularly preferably, the solid fatty acid(s) are chosen from lauric acid, myristic acid, cetylic acid (or palmitic acid), stearic acid and mixtures thereof, more preferentially from myristic acid, cetylic acid (or palmitic acid), stearic acid and mixtures thereof.

The term "fatty alcohol" means a long-chain aliphatic alcohol comprising from 6 to 40 carbon atoms, preferably from 8 to 30 carbon atoms, and comprising at least one hydroxyl group OH. These fatty alcohols are neither oxyalkylenated nor glycerolated.

The solid fatty alcohols may be saturated or unsaturated, and linear or branched, and include from 8 to 40 carbon atoms, preferably from 10 to 30 carbon atoms. Preferably, the solid fatty alcohols have the structure R—OH with R denoting a linear alkyl group, optionally substituted with one or more hydroxyl groups, comprising from 8 to 40, preferentially from 10 to 30 carbon atoms, better still from 10 to 30, or even from 12 to 24 atoms and even better still from 14 to 22 carbon atoms.

The solid fatty alcohols that may be used are preferably chosen from saturated or unsaturated, linear or branched, preferably linear and saturated, (mono)alcohols including from 8 to 40 carbon atoms, better still from 10 to 30, or even from 12 to 24 and even better still from 14 to 22 carbon atoms.

The solid fatty alcohols that may be used may be chosen, alone or as a mixture, from: myristyl alcohol (or 1-tetradecanol); cetyl alcohol (or 1-hexadecanol); stearyl alcohol (or 1-octadecanol); arachidyl alcohol (or 1-eicosanol); behenyl alcohol (or 1-docosanol); lignoceryl alcohol (or 1-tetracosanol); ceryl alcohol (or 1-hexacosanol); montanyl alcohol (or 1-octacosanol); myricyl alcohol (or 1-triacontanol).

Preferentially, the solid fatty alcohol is chosen from cetyl alcohol, stearyl alcohol, behenyl alcohol, myristyl alcohol, arachidyl alcohol, and mixtures thereof, such as cetylstearyl alcohol or cetearyl alcohol. Particularly preferably, the solid fatty alcohol is cetylstearyl alcohol or cetearyl alcohol.

The solid esters of a fatty acid and/or of a fatty alcohol that may be used are preferably chosen from esters derived from a C9-C26 carboxylic fatty acid and/or from a C9-C26 fatty alcohol.

Preferably, these solid fatty esters are esters of a linear or branched, saturated carboxylic acid including at least 10 carbon atoms, preferably from 10 to 30 carbon atoms and more particularly from 12 to 24 carbon atoms, and of a linear or branched, saturated monoalcohol, including at least 10 carbon atoms, preferably from 10 to 30 carbon atoms and more particularly from 12 to 24 carbon atoms. The saturated carboxylic acids may optionally be hydroxylated, and are preferably monocarboxylic acids.

Esters of C4-C22 dicarboxylic or tricarboxylic acids and of C1-C22 alcohols and esters of monocarboxylic, dicarboxylic or tricarboxylic acids and of C2-C26 dihydroxy, trihydroxy, tetrahydroxy or pentahydroxy alcohols may also be used.

Mention may notably be made of octyldodecyl behenate, isocetyl behenate, cetyl lactate, stearyl octanoate, octyl octanoate, cetyl octanoate, decyl oleate, hexyl stearate, octyl stearate, myristyl stearate, cetyl stearate, stearyl stearate, octyl pelargonate, cetyl myristate, myristyl myristate, stearyl myristate, diethyl sebacate, diisopropyl sebacate, diisopropyl adipate, di-n-propyl adipate, dioctyl adipate, dioctyl maleate, octyl palmitate, myristyl palmitate, cetyl palmitate, stearyl palmitate, and mixtures thereof.

Preferably, the solid esters of a fatty acid and/or of a fatty alcohol are chosen from C9-C26 alkyl palmitates, notably myristyl palmitate, cetyl palmitate or stearyl palmitate; C9-C26 alkyl myristates, such as cetyl myristate, stearyl myristate and myristyl myristate; and C9-C26 alkyl stearates, notably myristyl stearate, cetyl stearate and stearyl stearate; and mixtures thereof.

For the purposes of the present invention, a wax is a lipophilic compound, which is solid at 25° C. and atmospheric pressure, with a reversible solid/liquid change of state, having a melting point greater than about 40° C., which may be up to 200° C., and having in the solid state anisotropic crystal organization. In general, the size of the wax crystals is such that the crystals diffract and/or scatter light, giving the composition that comprises them a more or less opaque cloudy appearance. By bringing the wax to its melting point, it is possible to make it miscible with oils and to form a microscopically homogeneous mixture, but on returning the temperature of the mixture to room temperature, recrystallization of the wax, which is microscopically and macroscopically detectable (opalescence), is obtained.

In particular, the waxes that are suitable for use in the invention may be chosen from waxes of animal, plant or mineral origin, nonsilicone synthetic waxes, and mixtures thereof.

Mention may be made notably of hydrocarbon-based waxes, for instance beeswax, notably of organic origin, lanolin wax and Chinese insect waxes; rice bran wax, carnauba wax, candelilla wax, ouricury wax, esparto grass wax, berry wax, shellac wax, Japan wax and sumac wax; montan wax, orange wax and lemon wax, microcrystalline waxes, paraffins and ozokerite; polyethylene waxes, the waxes obtained by Fischer-Tropsch synthesis and waxy copolymers, and also esters thereof.

Mention may also be made of C20 to C60 microcrystalline waxes, such as Microwax HW.

Mention may also be made of the MW 500 polyethylene wax sold under the reference Permalen 50-L Polyethylene.

Mention may also be made of the waxes obtained by catalytic hydrogenation of animal or plant oils containing linear or branched C8 to C32 fatty chains. Among these waxes mention may notably be made of isomerized jojoba oil such as trans-isomerized partially hydrogenated jojoba oil, notably the product manufactured or sold by the company Desert Whale under the commercial reference Iso-Jojoba-50®, hydrogenated sunflower oil, hydrogenated castor oil, hydrogenated coconut kernel oil, hydrogenated lanolin oil and bis(1,1,1-trimethylolpropane)tetrastearate, notably the product sold under the name Hest 2T-4S® by the company Heterene.

The waxes obtained by hydrogenation of castor oil esterified with cetyl alcohol, such as those sold under the names Phytowax Castor 16L64® and 22L73® by the company Sophim, may also be used.

A wax that may also be used is a C20-C40 alkyl (hydroxystearyloxy)stearate (the alkyl group comprising from 20 to 40 carbon atoms), alone or as a mixture. Such a wax is notably sold under the names Kester Wax K 82 P®, Hydroxypolyester K 82 P® and Kester Wax K 80 P® by the company Koster Keunen.

It is also possible to use microwaxes in the compositions of the invention; mention may notably be made of carnauba microwaxes, such as the product sold under the name MicroCare 350® by the company Micro Powders, synthetic-wax microwaxes, such as the product sold under the name MicroEase 114S® by the company Micro Powders, microwaxes constituted of a mixture of carnauba wax and polyethylene wax, such as the products sold under the names Micro Care 300® and 310® by the company Micro Powders, microwaxes constituted of a mixture of carnauba wax and of synthetic wax, such as the product sold under the name Micro Care 325® by the company Micro Powders, polyethylene microwaxes, such as the products sold under the names Micropoly 200®, 220®, 220L® and 250S® by the company Micro Powders, and polytetrafluoroethylene microwaxes, such as the products sold under the names Microslip 519® and 519 L® by the company Micro Powders.

The waxes are preferably chosen from mineral waxes, for instance paraffin, petroleum jelly, lignite or ozokerite wax; plant waxes, for instance cocoa butter or cork fiber or sugar cane waxes, olive tree wax, rice wax, hydrogenated jojoba wax, ouricury wax, carnauba wax, candelilla wax, esparto grass wax, or absolute waxes of flowers, such as the essential wax of blackcurrant blossom sold by the company Bertin (France); waxes of animal origin, for instance beeswaxes or modified beeswaxes (cera bellina), spermaceti, lanolin wax and lanolin derivatives; microcrystalline waxes; and mixtures thereof.

The ceramides, or ceramide analogs such as glycoceramides, which may be used in the compositions according to the invention, are known; mention may be made in particular of ceramides of classes I, II, III and V according to the Dawning classification.

The ceramides or analogs thereof that may be used preferably correspond to the following formula: $R^3CH(OH)CH(CH_2OR^2)(NHCOR^1)$, in which:

$R^1$ denotes a linear or branched, saturated or unsaturated alkyl group, derived from $C_{14}$-$C_{30}$ fatty acids, this group possibly being substituted with a hydroxyl group in the alpha position, or a hydroxyl group in the omega position, esterified with a saturated or unsaturated $C_1$-$C_{30}$ fatty acid;

$R^2$ denotes a hydrogen atom, a (glycosyl)n group, a (galactosyl)m group or a sulfogalactosyl group, in which n is an integer ranging from 1 to 4 and m is an integer ranging from 1 to 8;

$R^3$ denotes a $C_{15}$-$C_{26}$ hydrocarbon-based group, saturated or unsaturated in the alpha position, this group possibly being substituted with one or more $C_1$-$C_{14}$ alkyl groups; it being understood that in the case of natural ceramides or glycoceramides, $R^3$ may also denote a $C_{15}$-$C_{26}$ alpha-hydroxyalkyl group, the hydroxyl group being optionally esterified with a $C_1$-$C_{30}$ alpha-hydroxy acid.

The ceramides that are more particularly preferred are the compounds for which $R^1$ denotes a saturated or unsaturated alkyl derived from $C_1$-$C_{22}$ fatty acids; $R^2$ denotes a hydrogen atom and $R^3$ denotes a saturated linear $C_{15}$ group.

Preferentially, use is made of ceramides for which $R^1$ denotes a saturated or unsaturated alkyl group derived from $C_{14}$-$C_{30}$ fatty acids; $R^2$ denotes a galactosyl or sulfogalactosyl group; and $R^3$ denotes a $—CH{=}CH—(CH_2)_{12}—CH_3$ group.

Use may also be made of compounds for which $R^1$ denotes a saturated or unsaturated alkyl radical derived from $C_{12}$-$C_{22}$ fatty acids; $R^2$ denotes a galactosyl or sulfogalactosyl radical and $R^3$ denotes a saturated or unsaturated $C_{12}$-$C_{22}$ hydrocarbon-based radical and preferably a $—CH{=}CH—(CH_2)_{12}—CH_3$ group.

As compounds that are particularly preferred, mention may also be made of 2-N-linoleoylaminooctadecane-1,3-diol; 2-N-oleoylaminooctadecane-1,3-diol; 2-N-palmitoylaminooctadecane-1,3-diol; 2-N-stearoylaminooctadecane-1,3-diol; 2-N-behenoylaminooctadecane-1,3-diol; 2-N-[2-hydroxypalmitoyl]aminooctadecane-1,3-diol; 2-N-stearoylaminooctadecane-1,3,4-triol and in particular N-stearoylphytosphingosine, 2-N-palmitoylaminohexadecane-1,3-diol, N-linoleoyldihydrosphingosine, N-oleoyldihydrosphingosine, N-palmitoyldihydrosphingosine, N-stearoyldihydrosphingosine, and N-behenoyldihydrosphingosine, N-docosanoyl-N-methyl-D-glucamine, cetylic acid N-(2-hydroxyethyl)-N-(3-cetyloxy-2-hydroxypropyl)amide and bis(N-hydroxyethyl-N-cetyl)malonamide; and mixtures thereof. N-Oleoyldihydrosphingosine will preferably be used.

The solid fatty substances are preferably chosen from solid fatty acids, solid fatty alcohols and mixtures thereof.

According to a preferred embodiment, the composition according to the invention comprises at least one liquid fatty substance, preferentially chosen from liquid hydrocarbons containing more than 16 carbon atoms, plant oils, liquid fatty alcohols, liquid fatty esters and mixtures thereof.

Preferentially, the composition according to the invention comprises at least one liquid fatty substance chosen from liquid hydrocarbons comprising more than 16 carbon atoms, in particular liquid petroleum jelly, liquid fatty alcohols, liquid fatty esters and mixtures thereof, more preferentially from liquid fatty esters.

According to another preferred embodiment, the composition according to the invention comprises at least one solid fatty substance, preferentially chosen from solid fatty acids, solid fatty alcohols and mixtures thereof.

According to another preferred embodiment, the composition according to the invention comprises at least one liquid fatty substance and at least one solid fatty substance, preferentially at least one liquid fatty ester, at least one solid fatty alcohol and at least one solid fatty acid.

When the composition according to the invention comprises one or more fatty substances other than (poly)oxyalkylenated amino silicones, the total content of the fatty substance(s) other than (poly)oxyalkylenated amino silicones preferably ranges from 5% to 60% by weight, more preferentially from 8% to 50% by weight and better still from 10% to 40% by weight, relative to the total weight of the composition.

Surfactants

The composition according to the present invention may comprise one or more surfactants. These surfactants may be chosen from anionic surfactants, nonionic surfactants, cationic surfactants, amphoteric or zwitterionic surfactants and mixtures thereof.

The term "anionic surfactant" means a surfactant including, as ionic or ionizable groups, only anionic groups. These anionic groups are preferably chosen from the following groups: $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2^-$, $PO_2^{2-}$, POH and $PO^-$.

As examples of anionic surfactants that can be used in the composition according to the invention, mention may be made of alkyl sulfates, alkyl ether sulfates, alkylamido ether sulfates, alkylaryl polyether sulfates, monoglyceride sulfates, alkyl sulfonates, alkylamide sulfonates, alkylaryl sulfonates, α-olefin sulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N—(C1-C4)alkyl-N-acyl taurates, salts of alkyl monoesters of polyglycoside-polycarboxylic acids, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds (unless otherwise mentioned) generally including from 6 to 24 carbon atoms and the aryl group generally denoting a phenyl group.

These compounds may be oxyethylenated and then preferably include from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts, such as the sodium or potassium and preferably sodium salt, ammonium salts, amine salts and in particular amino alcohol salts, or alkaline-earth metal salts, such as the magnesium salt.

Examples of amino alcohol salts that may notably be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

The anionic surfactants that may be present may be mild anionic surfactants, i.e. anionic surfactants not bearing a sulfate function.

As regards the mild anionic surfactants, mention may be made in particular of the following compounds and salts thereof, and also mixtures thereof: polyoxyalkylenated alkyl ether carboxylic acids, polyoxyalkylenated alkylaryl ether carboxylic acids, polyoxyalkylenated alkylamido ether carboxylic acids, in particular those including 2 to 50 ethylene oxide groups, alkyl D-galactoside uronic acids, acyl sarcosinates, acyl glutamates and alkylpolyglycoside carboxylic esters.

Use may be made most particularly of polyoxyalkylenated alkyl ether carboxylic acids, for instance lauryl ether carboxylic acid (4.5 OE) sold, for example, under the name Akypo RLM 45 CA from Kao.

Use is preferably made, among the abovementioned anionic surfactants, of sulfated surfactants, such as alkyl sulfates or alkyl ether sulfates, and acyl glutamates, more preferentially alkyl sulfates and/or alkyl ether sulfates, better still alkyl sulfates.

The nonionic surfactant(s) that may be used in the composition of the present invention are notably described, for example, in the "Handbook of Surfactants" by M. R. Porter, published by Blackie & Son (Glasgow and London), 1991, pages 116-178.

Examples of nonionic surfactants that may be mentioned include the following compounds, alone or as a mixture:

- oxyalkylenated ($C_8$-$C_{24}$)alkylphenols;
- saturated or unsaturated, linear or branched, oxyalkylenated or glycerolated $C_8$-$C_{40}$ alcohols, preferably including one or two fatty chains;
- saturated or unsaturated, linear or branched, oxyalkylenated $C_8$-$C_{30}$ fatty acid amides;
- esters of saturated or unsaturated, linear or branched, $C_8$-$C_{30}$ acids and of polyethylene glycols;
- fatty acid esters of sucrose;
- preferably oxyethylenated esters of saturated or unsaturated, linear or branched, $C_8$ to $C_{30}$ acids and of sorbitol;
- $C_8$-$C_{30}$ fatty acid esters of sorbitan;
- polyoxyethylenated $C_8$-$C_{30}$ fatty acid esters of sorbitan;
- ($C_8$-$C_{30}$)alkyl(poly)glucosides, ($C_8$-$C_3$)alkenyl(poly)glucosides, which are optionally oxyalkylenated (0 to 10 oxyalkylene units) and comprising from 1 to 15 glucose units, ($C_8$-$C_{30}$)alkyl(poly)glucoside esters;
- saturated or unsaturated oxyethylenated plant oils;
- condensates of ethylene oxide and/or of propylene oxide;
- N—($C_8$-$C_{30}$)alkylglucamine and N—($C_8$-$C_3$)acylmethylglucamine derivatives;
- amine oxides.

They are notably chosen from alcohols, α-diols and ($C_1$-$C_{20}$)alkylphenols, these compounds being ethoxylated, propoxylated or glycerolated and bearing at least one fatty chain including, for example, from 8 to 24 carbon atoms and preferably from 8 to 18 carbon atoms, the number of ethylene oxide or propylene oxide groups possibly ranging notably from 1 to 200, and the number of glycerol groups possibly ranging notably from 1 to 30.

Mention may also be made of condensates of ethylene oxide and of propylene oxide with fatty alcohols, ethoxylated fatty amides preferably containing from 1 to 30 ethylene oxide units, polyglycerolated fatty amides including on average from 1 to 5, and in particular from 1.5 to 4, glycerol groups, fatty acid esters of sucrose, fatty acid esters of polyethylene glycol, oxyethylenated plant oils, N—($C_6$-$C_{24}$ alkyl)glucamine derivatives, amine oxides such as ($C_{10}$-$C_{14}$ alkyl)amine oxides or N—($C_{10}$-$C_{14}$ acyl)aminopropylmorpholine oxides.

The $C_8$-$C_{30}$ and preferably $C_{12}$-$C_{22}$ fatty acid esters (notably monoesters, diesters and triesters) of sorbitan may be chosen from:

- sorbitan caprylate; sorbitan cocoate; sorbitan isostearate; sorbitan laurate; sorbitan oleate; sorbitan palmitate; sorbitan stearate; sorbitan diisostearate; sorbitan dioleate; sorbitan distearate; sorbitan sesquicaprylate; sorbitan sesquiisostearate; sorbitan sesquioleate; sorbitan sesquistearate; sorbitan triisostearate; sorbitan trioleate; and sorbitan tristearate.

The esters (notably monoesters, diesters, triesters) of $C_8$-$C_{30}$ fatty acids and of polyoxyethylenated sorbitan are preferably chosen from $C_8$-$C_{30}$ fatty acid ester(s) of oxyethylenated sorbitan containing from 1 to 30 ethylene oxide units, preferably from 2 to 20 ethylene oxide units, more preferably from 2 to 10 ethylene oxide units.

Preferentially, the $C_8$-$C_{30}$ fatty acid ester(s) of oxyethylenated sorbitan are chosen from esters of $C_{12}$-$C_{18}$ fatty acids and of oxyethylenated sorbitan, in particular from oxyethylenated esters of lauric acid, of myristic acid, of cetylic acid and of stearic acid and of sorbitan.

Preferably, the $C_8$-$C_{30}$ fatty acid ester(s) of oxyethylenated sorbitan are chosen from oxyethylenated (4 OE) sorbitan monolaurate (Polysorbate-21), oxyethylenated (20 OE) sorbitan monolaurate (Polysorbate-20), oxyethylenated (20 OE) sorbitan monopalmitate (Polysorbate-40), oxyethylenated (20 OE) sorbitan monostearate (Polysorbate-60), oxyethylenated (4 OE) sorbitan monostearate (Polysorbate-61), oxyethylenated (20 OE) sorbitan monooleate (Polysorbate-80), oxyethylenated (5 OE) sorbitan monooleate (Polysorbate-81), oxyethylenated (20 OE) sorbitan tristearate (Polysorbate-65), oxyethylenated (20 OE) sorbitan trioleate (Polysorbate-85).

The nonionic surfactant(s) are preferably chosen from ethoxylated $C_8$-$C_{24}$ fatty alcohols comprising from 1 to 200 ethylene oxide groups, saturated or unsaturated, linear or branched, oxyalkylenated amides of $C_8$-$C_{30}$ fatty acid, ($C_6$-$C_{24}$ alkyl)polyglycosides, esters of $C_8$-$C_{30}$ fatty acids and of oxyethylenated sorbitan, and mixtures thereof, more preferentially ethoxylated $C_8$-$C_{24}$ fatty alcohols comprising from 1 to 200 ethylene oxide groups.

The cationic surfactant(s) that may be used in the composition according to the invention are generally chosen from optionally polyoxyalkylenated primary, secondary or tertiary fatty amines, quaternary ammonium salts, and mixtures thereof.

The fatty amines generally comprise at least one $C_8$-$C_{30}$ hydrocarbon-based chain. Among the fatty amines that may be used according to the invention, examples that may be mentioned include stearylamidopropyldimethylamine and distearylamine.

Examples of quaternary ammonium salts that may notably be mentioned include:

those corresponding to the general formula (VI) below:

(VI)

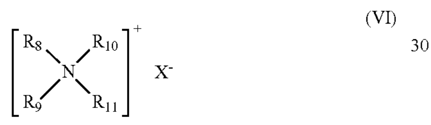

in which the groups $R_8$ to $R_{11}$, which may be identical or different, represent a linear or branched aliphatic group including from 1 to 30 carbon atoms, or an aromatic group such as aryl or alkylaryl, at least one of the groups $R_8$ to $R_{11}$ including from 8 to 30 carbon atoms and preferably from 12 to 24 carbon atoms. The aliphatic groups may include heteroatoms notably such as oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates and ($C_1$-$C_4$)alkylsulfonates or ($C_1$-$C_4$)alkylarylsulfonates.

Among the quaternary ammonium salts of formula (VI), preference is given, firstly, to tetraalkylammonium chlorides, for instance dialkyldimethylammonium or alkyltrimethylammonium chlorides in which the alkyl group includes from about 12 to 22 carbon atoms, in particular behenyltrimethylammonium chloride, distearyldimethylammonium chloride, cetyltrimethylammonium chloride or benzyldimethylstearylammonium chloride, or, secondly, to distearoylethylhydroxyethylmethylammonium methosulfate, dipalmitoylethylhydroxyethylammonium methosulfate or distearoylethylhydroxyethylammonium methosulfate, or also, finally, to palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (VII) below:

(VII)

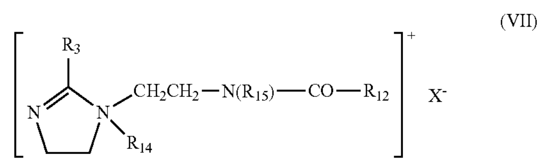

in which R12 represents an alkenyl or alkyl group including from 8 to 30 carbon atoms, for example tallow fatty acid derivatives, R13 represents a hydrogen atom, a $C_1$-$C_4$ alkyl group or an alkenyl or alkyl group including from 8 to 30 carbon atoms, R14 represents a $C_1$-$C_4$ alkyl group, R15 represents a hydrogen atom or a $C_1$-$C_4$ alkyl group, and $X^-$ is an anion chosen from the group of halides, phosphates, acetates, lactates, ($C_1$-$C_4$)alkyl sulfates, and ($C_1$-$C_4$)alkylsulfonates or ($C_1$-$C_4$)alkylarylsulfonates.

Preferably, R12 and R13 denote a mixture of alkenyl or alkyl groups including from 12 to 21 carbon atoms, for example tallow fatty acid derivatives, R14 denotes a methyl group and R15 denotes a hydrogen atom. Such a product is sold, for example, under the name Rewoquat® W 75 by the company Rewo, quaternary diammonium or triammonium salts, in particular of formula (VIII) below:

(VIII)

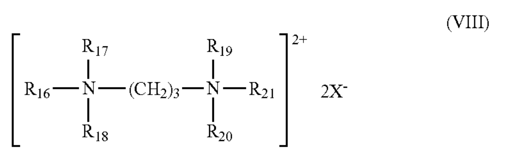

in which R16 denotes an alkyl group including from about 16 to 30 carbon atoms, which is optionally hydroxylated and/or interrupted with one or more oxygen atoms; R17 is chosen from hydrogen, an alkyl group including from 1 to 4 carbon atoms or a group —$(CH_2)_3$—$N^+$(R16a)(R17a)(R18a), R16a, R17a, R18a, R18, R19, R20 and R21, which may be identical or different, are chosen from hydrogen or an alkyl group including from 1 to 4 carbon atoms, and X— is an anion chosen from the group of halides, acetates, phosphates, nitrates, ($C_1$-$C_4$)alkyl sulfates, ($C_1$-$C_4$)alkylsulfonates or ($C_1$-$C_4$)alkylarylsulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts containing one or more ester functions, for instance those of formula (IX) below:

(IX)

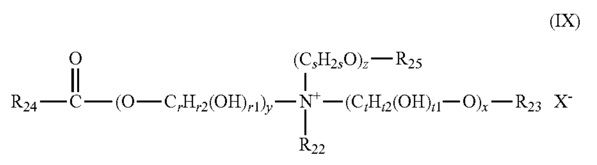

in which: R22 is chosen from $C_1$-$C_6$ alkyl groups and $C_1$-$C_6$ hydroxyalkyl or dihydroxyalkyl groups; R23 is chosen from: the group —C(O)R26, linear or branched, saturated or unsaturated $C_1$-$C_{22}$ hydrocarbon-based groups R27, or a hydrogen atom; R25 is chosen from: the group —C(O)R28, linear or branched, saturated or unsaturated $C_1$-$C_6$ hydrocarbon-based groups R29, or a hydrogen atom; R24, R26 and R28, which may be identical or different, are chosen from linear or branched, saturated or unsaturated $C_7$-$C_{21}$ hydrocarbon-based groups; r, s and t, which may be identical or different, are integers from 2 to 6; r1 and t1, which may be identical or different, are 0 or 1; r2+r1=2 r and t1+t2=2 t, y is an integer from 1 to 10, x and z, which may be identical or different, are integers from 0 to 10, $X^-$ is an organic or inorganic simple or complex anion, with the proviso that the sum x+y+z is from 1 to 15, that when x is 0, R23 denotes R27 and that when z is 0, R25 denotes R29.

The alkyl groups R22 may be linear or branched, and more particularly linear.

Preferably, R22 denotes a methyl, ethyl, hydroxyethyl or dihydroxypropyl group, and more particularly a methyl or ethyl group.

Advantageously, the sum x+y+z is from 1 to 10.

When R23 is a hydrocarbon-based group R27, it may be long and may contain 12 to 22 carbon atoms, or may be short and may contain from 1 to 3 carbon atoms.

When R25 is a hydrocarbon-based group R29, it preferably contains 1 to 3 carbon atoms.

Advantageously, R24, R26 and R28, which may be identical or different, are chosen from linear or branched, saturated or unsaturated C11-C21 hydrocarbon-based groups, and more particularly from linear or branched, saturated or unsaturated C11-C21 alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide, preferably chloride, bromide or iodide, a (C1-C4)alkyl sulfate or a (C1-C4)alkyl- or (C1-C4)alkylaryl-sulfonate. However, use may be made of methanesulfonate, phosphate, nitrate, tosylate, an anion derived from an organic acid, such as acetate or lactate, or any other anion that is compatible with the ammonium bearing an ester function.

The anion $X^-$ is even more particularly chloride, methyl sulfate or ethyl sulfate.

Use is made more particularly, in the composition according to the invention, of the ammonium salts of formula (XIII) in which: R22 denotes a methyl or ethyl group, x and y are equal to 1, z is equal to 0 or 1, r, s and t are equal to 2; R23 is chosen from: the group —C(O)R26, methyl, ethyl or C14-C22 hydrocarbon-based groups, or a hydrogen atom, R25 is chosen from: the group —C(O)R28, or a hydrogen atom, R24, R26 and R28, which may be identical or different, are chosen from linear or branched, saturated or unsaturated C13-C17 hydrocarbon-based groups, and preferably from linear or branched, saturated or unsaturated C13-C17 alkyl and alkenyl groups.

Advantageously, the hydrocarbon-based groups are linear.

Among the compounds of formula (XIII), examples that may be mentioned include salts, notably the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are derived more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by quaternization by means of an alkylating agent such as an alkyl halide, preferably a methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in patents U.S. Pat. Nos. 4,874,554 and 4,137,180.

Use may also be made of the behenoylhydroxypropyltrimethylammonium chloride sold, for example, by the company Kao under the name Quartamin BTC 131.

Preferably, the ammonium salts containing at least one ester function contain two ester functions.

Among the cationic surfactants, it is more particularly preferred to choose cetyltrimethylammonium, behenyltrimethylammonium and dipalmitoylethylhydroxyethyl-methylammonium salts, and mixtures thereof, and more particularly behenyltrimethylammonium chloride, cetyltrimethylammonium chloride, and dipalmitoylethylhydroxyethylammonium methosulfate, and mixtures thereof.

The amphoteric or zwitterionic surfactant(s), preferably non-silicone amphoteric or zwitterionic surfactant(s), used in the composition according to the present invention may notably be optionally quaternized secondary or tertiary aliphatic amine derivatives, in which the aliphatic group is a linear or branched chain including from 8 to 22 carbon atoms, said amine derivatives containing at least one anionic group, for instance a carboxylate, sulfonate, sulfate, phosphate or phosphonate group.

Mention may in particular be made of ($C_8$-$C_{20}$)alkylbetaines, ($C_8$-$C_2$)alkylsulfobetaines, ($C_8$-$C_{20}$)alkylamido($C_1$-$C_6$)alkylbetaines and ($C_8$-$C_{20}$)alkylamido($C_1$-$C_6$)alkylsulfobetaines, and mixtures thereof.

Among the optionally quaternized secondary or tertiary aliphatic amine derivatives that may be used, as defined above, mention may also be made of the compounds having the respective structures (X) and (XI) below:

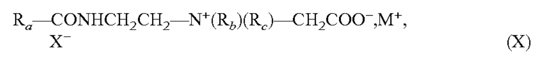

$$R_a\text{—CONHCH}_2\text{CH}_2\text{—N}^+(R_b)(R_c)\text{—CH}_2\text{COO}^-,M^+,X^- \quad (X)$$

in which formula (X):

- $R_a$ represents a $C_{10}$ to $C_{30}$ alkyl or alkenyl group derived from an acid $R_a$COOH preferably present in hydrolyzed coconut kernel oil; preferably, $R_a$ represents a heptyl, nonyl or undecyl group;
- $R_b$ represents a β-hydroxyethyl group;
- $R_c$ represents a carboxymethyl group;
- $M^+$ represents a cationic counterion derived from an alkali metal or alkaline-earth metal, such as sodium, an ammonium ion or an ion derived from an organic amine; and
- $X^-$ represents an organic or mineral anionic counterion, such as that chosen from halides, acetates, phosphates, nitrates, $(C_1\text{-}C_4)$alkyl sulfates, $(C_1\text{-}C_4)$alkyl- or $(C_1\text{-}C_4)$alkylaryl-sulfonates, in particular methyl sulfate and ethyl sulfate; or alternatively $M^+$ and $X^-$ are absent;

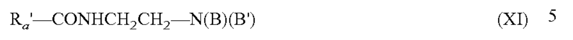

$R_a'\text{—}CONHCH_2CH_2\text{—}N(B)(B')$ (XI)

in which formula (XI):

B represents the group $\text{—}CH_2CH_2OX'$;

B' represents the group $\text{—}(CH_2)_zY'$, with z=1 or 2;

X' represents the group $\text{—}CH_2COOH$, $\text{—}CH_2\text{—}COOZ'$, $\text{—}CH_2CH_2COOH$ or $CH_2CH_2\text{—}COOZ'$, or a hydrogen atom;

Y' represents the group —COOH, —COOZ' or $\text{—}CH_2CH(OH)SO_3H$ or the group $CH_2CH(OH)SO_3\text{—}Z'$;

Z' represents a cationic counterion derived from an alkali metal or alkaline-earth metal, such as sodium, an ammonium ion or an ion derived from an organic amine;

$R_{a'}$ represents a $C_{10}$ to $C_{30}$ alkyl or alkenyl group of an acid $R_{a'}\text{—}COOH$ which is preferably present in coconut kernel oil or in hydrolyzed linseed oil, preferably $R_{a'}$ an alkyl group, notably a $C_{17}$ group, and its iso form, an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Use may also be made of compounds of formula (XII):

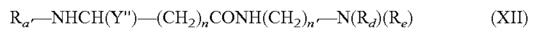

$R_{a''}\text{—}NHCH(Y'')\text{—}(CH_2)_nCONH(CH_2)_{n'}\text{—}N(R_d)(R_e)$ (XII)

in which formula (XII):

Y" represents the group —COOH, —COOZ" or $\text{—}CH_2\text{—}CH(OH)SO_3H$ or the group $CH_2CH(OH)SO_3\text{—}Z''$;

$R_d$ and $R_e$, independently of each other, represent a $C_1$ to $C_4$ alkyl or hydroxyalkyl radical;

Z" represents a cationic counterion derived from an alkali metal or alkaline-earth metal, such as sodium, an ammonium ion or an ion derived from an organic amine;

$R_{a''}$— represents a $C_{10}$ to $C_{30}$ alkyl or alkenyl group of an acid $R_{a''}\text{—}COOH$ which is preferably present in coconut kernel oil or in hydrolyzed linseed oil; and n and n' denote, independently of each other, an integer ranging from 1 to 3.

Among the compounds of formula (XII), mention may be made of the compound classified in the CTFA dictionary under the name sodium diethylaminopropyl cocoaspartamide and sold by the company Chimex under the name Chimexane HB.

These compounds may be used alone or as mixtures.

Among the amphoteric or zwitterionic surfactants mentioned above, use is advantageously made of $(C_8\text{-}C_{20})$alkylbetaines, such as cocoyl betaine, $(C_8\text{-}C_{20})$alkylamido$(C_3\text{-}C_8)$alkylbetaines, such as cocamidopropylbetaine, $(C_8\text{-}C_2)$alkylamphoacetates, $(C_8\text{-}C_2)$alkylamphodiacetates and mixtures thereof; and preferably $(C_8\text{-}C_{20})$alkylbetaines, $(C_8\text{-}C_{20})$alkylamido$(C_3\text{-}C_8)$alkylbetaines and mixtures thereof.

Preferentially, the amphoteric or zwitterionic surfactant(s) are chosen from $(C_8\text{-}C_{20})$alkylbetaines, $(C_8\text{-}C_{20})$alkylamido$(C_3\text{-}C_8)$alkylbetaines, and mixtures thereof.

Preferably, the surfactant(s) are chosen from anionic surfactants, nonionic surfactants, cationic surfactants and mixtures thereof.

Preferably, the composition according to the invention comprises one or more surfactants, preferably chosen from anionic surfactants, nonionic surfactants, cationic surfactants, and mixtures thereof, preferably from anionic surfactants, nonionic surfactants and mixtures thereof, preferably from anionic surfactants.

When the composition comprises one or more surfactant(s), the total content of surfactant(s) in the composition preferably ranges from 0.01% to 25% by weight, more preferentially from 0.1% to 20% by weight, better still from 0.5% to 15% by weight, even better still from 1% to 10% by weight, relative to the total weight of the composition.

Cationic Polymer

The composition according to the invention may also comprise one or more cationic polymers.

For the purposes of the present invention, the term "cationic polymer" denotes any polymer containing cationic groups and/or groups that can be ionized into cationic groups.

Preferably, the cationic polymers according to the invention do not comprise any anionic and/or anionizable groups.

The cationic polymer(s) that may be present in the composition according to the invention may be chosen from any of those already known per se as improving the cosmetic properties of the hair, i.e. notably those described in patent application EP-A-337 354 and in French patents FR-2 270 846, 2 383 660, 2 598 611, 2 470 596 and 2 519 863.

The cationic polymers used generally have a number-average molecular mass of between 500 and $5\times10^6$ approximately and preferably between $10^3$ and $3\times10^6$ approximately.

Among the cationic polymers that may be mentioned more particularly are polymers of the polyamine, polyaminoamide and polyquaternary ammonium type.

These are known products. They are notably described in French patents 2 505 348 and 2 542 997.

The cationic polymer(s) that may be used in the composition according to the invention may be chosen from:

(1) Homopolymers or copolymers derived from acrylic or methacrylic esters or amides and including at least one of the units of formula (XIII), (XIV), (XV) or (XVI) below:

(XIII)

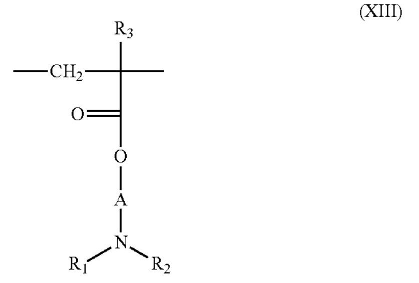

(XIV)

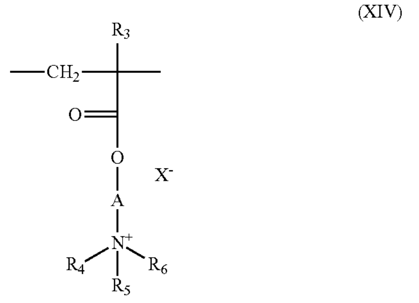

-continued (XV)

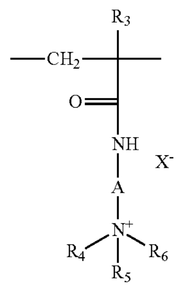

(XVI)

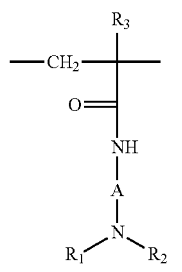

in which:

$R_3$, which may be identical or different, denote a hydrogen atom or a $CH_3$ radical;

A, which may be identical or different, represent a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl radical and preferably an alkyl group containing from 1 to 6 carbon atoms;

$R_1$ and $R_2$, which may be identical or different, represent hydrogen or an alkyl group containing from 1 to 6 carbon atoms, and preferably methyl or ethyl;

X denotes an anion derived from a mineral or organic acid, such as a methosulfate anion or a halide such as chloride or bromide.

Mention may be made in particular of the ethyltrimethylammonium methacrylate chloride homopolymer.

The polymers of family (1) may also contain one or more units derived from comonomers which may be chosen from the family of acrylamides, methacrylamides, diacetone acrylamides, acrylamides and methacrylamides substituted on the nitrogen with lower (C1-C4)alkyls, acrylic or methacrylic acids or esters thereof, vinyllactams such as vinylpyrrolidone or vinylcaprolactam, and vinyl esters.

Thus, among these polymers of family (1), mention may be made of:

copolymers of acrylamide and of dimethylaminoethyl methacrylate quaternized with dimethyl sulfate or with a dimethyl halide, such as the product sold under the name Hercofloc by the company Hercules, copolymers of acrylamide and of methacryloyloxyethyltrimethylammonium chloride, described, for example, in patent application EP-A-080 976 and sold under the name Bina Quat P 100 by the company Ciba Geigy, the copolymer of acrylamide and of methacryloyloxyethyltrimethylammonium methosulfate sold under the name Reten by the company Hercules, quaternized or non-quaternized vinylpyrrolidone/dialkylaminoalkyl acrylate or methacrylate copolymers, such as the products sold under the name Gafquat by the company ISP, for instance Gafquat 734 or Gafquat 755, or alternatively the products known as Copolymer 845, 958 and 937.

These polymers are described in detail in French patents 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, quaternized vinylpyrrolidone/dimethylaminopropylmethacrylamide copolymers such as the product sold under the name Gafquat HS 100 by the company ISP, crosslinked polymers of methacryloyloxy(C1-C4)alkyltri(C1-C4)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, more particularly methylenebisacrylamide. Use may more particularly be made of a crosslinked acrylamide/methacryloyloxyethyltrimethylammonium chloride copolymer (20/80 by weight) in the form of a dispersion containing 50% by weight of said copolymer in mineral oil. This dispersion is sold under the name Salcare® SC 92 by the company Ciba. Use may also be made of a crosslinked homopolymer of methacryloyloxyethyltrimethylammonium chloride comprising approximately 50% by weight of the homopolymer in mineral oil or in a liquid ester. These dispersions are sold under the names Salcare® SC 95 and Salcare® SC 96 by the company Ciba.

(2) The cellulose ether derivatives including quaternary ammonium groups, described in French patent 1 492 597, and in particular the polymers sold under the names "Ucare Polymer JR" (JR 400 LT, JR 125 and JR 30M) or "LR" (LR 400 or LR 30M) by the company Amerchol. These polymers are also defined in the CTFA dictionary as quaternary ammoniums of hydroxyethylcellulose that have reacted with an epoxide substituted with a trimethylammonium group.

(3) Copolymers of cellulose or cellulose derivatives grafted with a water-soluble quaternary ammonium monomer, notably described in U.S. Pat. No. 4,131,576, such as hydroxyalkylcelluloses, for instance hydroxymethyl-, hydroxyethyl- or hydroxypropylcelluloses notably grafted with a methacryloylethyltrimethyl-ammonium, methacrylamidopropyltrimethylammonium or dimethyldiallyl-ammonium salt.

The commercial products corresponding to this definition are more particularly the products sold under the names Celquat L 200 and Celquat H 100 by the company National Starch.

(4) Cationic guar gums, in particular those described more particularly in U.S. Pat. No. 3,589,578 and 4 031307, such as guar gums containing cationic trialkylammonium groups. Guar gums modified with a salt (e.g. chloride) of 2,3-epoxypropyltrimethylammonium are used, for example.

Such products are notably sold under the trade names Jaguar C13 S, Jaguar C 15, Jaguar C 17 and Jaguar C162 by the company Rhodia.

(5) Polymers formed from piperazinyl units and divalent alkylene or hydroxyalkylene radicals bearing straight or branched chains, optionally interrupted with oxygen, sulfur or nitrogen atoms or with aromatic or heterocyclic rings, and also the oxidation and/or quaternization products of these polymers. Such polymers are notably described in French patents 2 162 025 and 2 280 361.

(6) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they include one or more tertiary amine functions, they can be quaternized. Such polymers are notably described in French patents 2 252 840 and 2 368 508.

(7) Polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical includes from 1 to 4 carbon atoms and preferably denotes methyl, ethyl or propyl. Such polymers are notably described in French patent 1 583 363.

Among these derivatives, mention may be made more particularly of the adipic acid/dimethylaminohydroxypropyl/diethylenetriamine polymers sold under the name Cartaretine F, F4 or F8 by the company Sandoz.

(8) Polymers obtained by reacting a polyalkylene polyamine including two primary amine groups and at least one secondary amine group with a dicarboxylic acid chosen from diglycolic acid and saturated aliphatic dicarboxylic acids containing from 3 to 8 carbon atoms. The mole ratio between the polyalkylenepolyamine and the dicarboxylic acid is between 0.8:1 and 1.4:1; the polyaminoamide resulting therefrom is reacted with epichlorohydrin in a mole ratio of epichlorohydrin relative to the secondary amine group of the polyaminoamide of between 0.5:1 and 1.8:1. Such polymers are notably described in U.S. Pat. No. 3,227,615 and 2 961347.

Polymers of this type are sold in particular under the name Hercosett 57 by the company Hercules Inc. or else under the name PD 170 or Delsette 101 by the company Hercules in the case of the adipic acid/epoxypropyl/diethylenetriamine copolymer.

(9) Cyclopolymers of alkyldiallylamine or of dialkyldiallylammonium, such as the homopolymers or copolymers including, as main constituent of the chain, units corresponding to formula (XVII) or (XVIII):

(XVII)

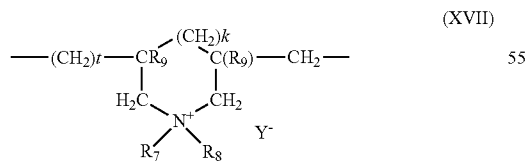

(XVIII)

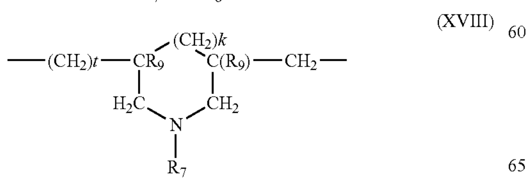

in which formulae k and t are equal to 0 or 1, the sum k+t being equal to 1;

R9 denotes a hydrogen atom or a methyl radical;

R7 and R8, independently of each other, denote an alkyl group containing from 1 to 6 carbon atoms, a hydroxyalkyl group in which the alkyl group preferably contains 1 to 5 carbon atoms, or a lower (C1-C4) amidoalkyl group, or R7 and R8 may denote, together with the nitrogen atom to which they are attached, heterocyclic groups, such as piperidyl or morpholinyl; R7 and R8, independently of each other, preferably denote an alkyl group containing from 1 to 4 carbon atoms;

$Y^-$ is an anion such as bromide, chloride, acetate, borate, citrate, tartrate, bisulfate, bisulfite, sulfate or phosphate. These polymers are in particular described in French patent 2 080 759 and in its Certificate of Addition 2 190 406.

Among the polymers defined above, mention may be made more particularly of the dimethyldiallylammonium chloride homopolymer sold under the name Merquat 100 by the company Nalco (and its homologs of low weight-average molecular mass), and the copolymers of diallyldimethylammonium chloride and of acrylamide sold under the names Merquat 550 and Merquat 7SPR.

(10) Quaternary diammonium polymers containing repeating units corresponding to formula (XIX) below:

(XIX)

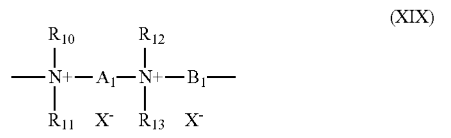

in which:

R10, R11, R12 and R13, which may be identical or different, represent aliphatic, alicyclic or arylaliphatic radicals containing from 1 to 6 carbon atoms or lower hydroxyalkylaliphatic radicals, or alternatively R10, R11, R12 and R13, together or separately, constitute, with the nitrogen atoms to which they are attached, heterocycles optionally containing a second heteroatom other than nitrogen, or alternatively R10, R11, R12 and R13 represent a linear or branched $C_1$-$C_6$ alkyl radical substituted with a nitrile, ester, acyl or amide group or a group COOR14D or CONHR14D where R14 is an alkylene and D is a quaternary ammonium group;

A1 and B1 represent polymethylene groups containing from 2 to 8 carbon atoms, which may be linear or branched and saturated or unsaturated and may contain, bonded to or intercalated in the main chain, one or more aromatic rings, or one or more oxygen or sulfur atoms, or sulfoxide, sulfone, disulfide, amino, alkylamino, hydroxyl, quaternary ammonium, ureido, amide or ester groups, and $X^-$ denotes an anion derived from a mineral or organic acid;

A1, R10 and R12 can form, with the two nitrogen atoms to which they are attached, a piperazine ring; in addition, if A1 denotes a linear or branched, saturated or unsaturated alkylene or hydroxyalkylene radical, B1 can also denote a group —(CH2)n-CO-D-OC—(CH2)n- in which D denotes:

a) a glycol residue of formula: —O—Z—O—, where Z denotes a linear or branched hydrocarbon-based radical or a group corresponding to one of the following formulae:

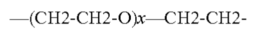

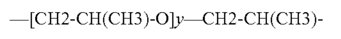

in which x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula: —NH—Y—NH—, where Y denotes a linear or branched hydrocarbon-based radical, or else the divalent radical

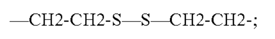

d) a ureylene group of formula: —NH—CO—NH—.

Preferably, $X^-$ is an anion, such as chloride or bromide.

These polymers have a number-average molecular mass generally between 1000 and 100 000.

Polymers of this type are notably described in French patents 2 320 330, 2 270 846, 2 316 271, 2 336 434 and 2 413 907 and U.S. Pat. Nos. 2,273,780, 2 375 853, 2 388 614, 2 454 547, 3 206 462, 2 261002, 2 271378, 3 874 870, 4 001432, 3 929 990, 3 966 904, 4 005 193, 4 025 617, 4 025 627, 4 025 653, 4 026 945 and 4 027 020.

It is more particularly possible to use polymers that are constituted of repeating units corresponding to formula (XX) below:

(XX)

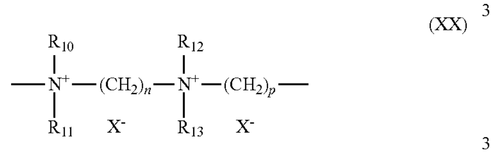

in which R10, R11, R12 and R13, which may be identical or different, denote an alkyl or hydroxyalkyl radical containing from 1 to 4 carbon atoms approximately, n and p are integers ranging from 2 to 8 approximately, and $X^-$ is an anion derived from a mineral or organic acid. Mention may be made in particular of Mexomere PO sold by the company Chimex.

(11) Polyquaternary ammoniums formed from repeating units of formula (XXI):

(XXI)

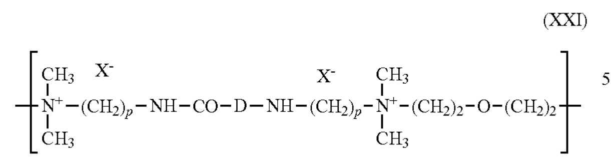

in which p denotes an integer ranging from 1 to 6 approximately, D may be nothing or may represent a group —(CH2) r—CO— in which r denotes a number equal to 4 or 7, and $X^-$ is an anion.

Such polymers may be prepared according to the processes described in U.S. Pat. Nos. 4,157,388, 4 702 906 and 4 719 282. They are notably described in patent application EP-A-122 324.

Among these polymers, examples that may be mentioned include the products Mirapol A 15, Mirapol AD1, Mirapol AZ1 and Mirapol 175 sold by the company Miranol.

(12) Quaternary polymers of vinylpyrrolidone and of vinylimidazole, for instance the products sold under the names Luviquat FC 905, FC 550 and FC 370 by the company BASF. These polymers may also comprise other monomers, such as diallyldialkylammonium halides. Mention may be made in particular of the product sold under the name Luviquat Sensation by the company BASF.

(13) Cationic polyamines such as Polyquart H sold by Henkel, which is referenced under the name Polyethylene Glycol (15) Tallow Polyamine in the CTFA dictionary, or oxyethylenated (15 OE) coconut kernel polyamines.

Other cationic polymers that may be used in the context of the invention are polyalkyleneimines, in particular polyethyleneimines, polymers containing vinylpyridine or vinylpyridinium units, condensates of polyamines and epichlorohydrin, quaternary polyureylenes and chitin derivatives.

Among all the cationic polymers that may be used in the context of the present invention, it is preferable to use polymers of the families (1), (2), (3), (4), (9), (10) and (12), more particularly polymers of the families (2), (3), (4) and (9), and more preferably polymers of the family (9).

Even more preferentially, the cationic polymer(s) used in the cosmetic composition according to the invention are chosen from dimethyldiallylammonium chloride homopolymers and diallyldimethylammonium chloride/acrylamide copolymers, and even more preferentially the cationic polymer is dimethyldiallylammonium chloride homopolymer (polyquaternium-6).

Preferably, the composition according to the invention comprises one or more cationic polymers.

When the composition comprises one or more cationic polymer(s), the total content of cationic polymer(s) in the composition preferably ranges from 0.01% to 10% by weight, preferably from 0.05% to 8% by weight, more preferentially from 0.1% to 5% by weight, and even better still from 0.2% to 2% by weight, relative to the total weight of the composition according to the invention.

Alkaline Agent

The composition according to the present invention may comprise one or more mineral, organic or hybrid alkaline agents.

Preferably, the composition according to the present invention comprises one or more mineral, organic or hybrid alkaline agents.

For the purposes of the present invention, the terms "alkaline agent" and "basifying agent" are used interchangeably.

The mineral basifying agent(s) are preferably chosen from ammonium hydroxide, alkali metal carbonates or bicarbonates such as sodium (hydrogen)carbonate and potassium (hydrogen)carbonate, alkali metal or alkaline-earth metal phosphates such as sodium phosphates or potassium phosphates, sodium or potassium hydroxides, and mixtures thereof.

The organic basifying agent(s) are preferably chosen from alkanolamines, amino acids, organic amines, oxyethylenated and/or oxypropylenated ethylenediamines, 1,3-diaminopropane, 1,3-diamino-2-propanol, spermine, spermidine and mixtures thereof.

The term "alkanolamine" means an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

In particular, the alkanolamine(s) are chosen from monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethyl)aminomethane and mixtures thereof.

Advantageously, the amino acids are basic amino acids comprising an additional amine function. Such basic amino acids are preferably chosen from histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole. The organic amine may also be chosen from amino acid dipeptides. As amino acid dipeptides that may be used in the present invention, mention may notably be made of carnosine, anserine and balenine. The organic amine may also be chosen from compounds including a guanidine function. As amines of this type other than arginine that may be used in the present invention, mention may notably be made of creatine, creatinine, 1,1-dimethylguanidine, 1,1-diethylguanidine, glycocyamine, metformin, agmatine, n-amidoalanine, 3-guanidinopropionic acid, 4-guanidinobutyric acid and 2-([amino(imino)methyl]amino)ethane-1-sulfonic acid.

Use may be made in particular of guanidine carbonate or monoethanolamine hydrochloride as hybrid compounds.

The alkaline agent(s) that are useful according to the invention is(are) preferably chosen from alkanolamines such as monoethanolamine, diethanolamine or triethanolamine; ammonium hydroxide, sodium hydroxides or potassium hydroxides, and mixtures thereof, more preferentially from ammonium hydroxide, sodium hydroxides or potassium hydroxides and mixtures thereof.

According to a preferred embodiment, the composition comprises ammonium hydroxide.

When the composition comprises at least one alkaline agent, the total content of the alkaline agent(s) preferably ranges from 0.1% to 40% by weight, more preferentially from 0.5% to 30% by weight, better still from 0.5% to 20% by weight, even better still from 1% to 15% by weight, relative to the total weight of the composition.

According to one embodiment, when the composition is aqueous, the pH of the composition according to the invention is between 8 and 13, preferably between 9 and 12.

The pH of the composition may be adjusted to the desired value by means of acidic or alkaline agent(s) commonly used in the dyeing of keratin fibers, such as those described previously, or alternatively using buffer systems that are known to those skilled in the art.

Solvents

The composition according to the invention may also comprise at least one organic solvent.

Examples of organic solvents that may be mentioned include linear or branched $C_2$ to $C_4$ alkanols, such as ethanol and isopropanol; polyols and polyol ethers, for instance glycerol, 2-butoxyethanol, propylene glycol, dipropylene glycol, propane-1,3-diol, propylene glycol monomethyl ether, diethylene glycol monomethyl ether and monoethyl ether, and also aromatic alcohols or ethers, such as benzyl alcohol or phenoxyethanol, and mixtures thereof.

Preferably, the composition comprises at least one organic solvent chosen from glycerin, propylene glycol, dipropylene glycol, propane-1,3-diol and mixtures thereof.

The organic solvent(s) may be present in a total amount ranging from 0.01% to 30% by weight, preferably ranging from 0.1% to 25% by weight, preferentially from 1% to 20% by weight, relative to the total weight of the composition.

In addition, the composition according to the invention is preferably an aqueous composition. The composition preferably comprises water in an amount of greater than or equal to 15% by weight, preferably greater than or equal to 30% by weight, and better still greater than or equal to 50% by weight, relative to the total weight of the composition.

Additives

The composition according to the invention may optionally comprise one or more additives, other than the compounds of the invention, and among which mention may be made of anionic or nonionic polymers or mixtures thereof, mineral thickeners, antidandruff agents, anti-seborrhoeic agents, agents for preventing hair loss and/or for promoting hair regrowth, vitamins and provitamins including panthenol, sunscreens, mineral or organic pigments, plasticizers, solubilizers, opacifiers or nacreous agents, antioxidants, hydroxy acids, fragrances, preserving agents and sequestrants.

Needless to say, a person skilled in the art will take care to select this or these optional additional compounds such that the advantageous properties intrinsically associated with the composition according to the invention are not, or are not substantially, adversely affected by the envisaged addition(s).

The above additives may generally be present in an amount, for each of them, of between 0 and 20% by weight relative to the total weight of the composition.

Preferably, the composition according to the invention does not comprise any chemical oxidizing agents.

According to a particular embodiment, the composition according to the invention comprises:

at least one oxidation base chosen from the derivatives of para-phenylenediamine of formula (I), addition salts thereof, solvates thereof and/or solvates of the salts thereof:

(I)

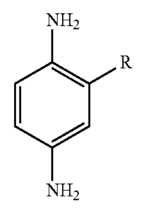

in which R is chosen from:

i) a $(C_1-C_4)$alkoxy$(C_1-C_4)$alkyl radical, ii) a $C_1-C_4$ hydroxyalkyl radical;

at least one oxidation coupler chosen from 6-hydroxybenzomorpholine of formula (II), an addition salt thereof, solvates thereof and/or solvates of the salts thereof and mixtures thereof:

(II)

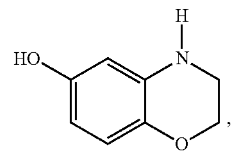

at least one (poly)oxyalkylenated amino silicone, and
at least one alkaline agent.

According to another particular embodiment, the composition according to the invention comprises:

at least one oxidation base chosen from the derivatives of para-phenylenediamine of formula (I), addition salts thereof, solvates thereof and/or solvates of the salts thereof:

(I)

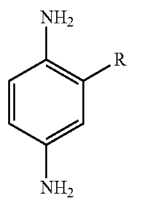

in which R is chosen from:
i) a $(C_1-C_4)$alkoxy$(C_1-C_4)$alkyl radical,
ii) a $C_1-C_4$ hydroxyalkyl radical;

at least one oxidation coupler chosen from 6-hydroxybenzomorpholine of formula (II), an addition salt thereof, solvates thereof and/or solvates of the salts thereof and mixtures thereof:

(II)

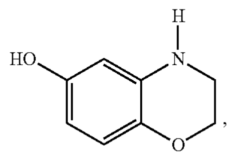

at least one (poly)oxyalkylenated amino silicone,
at least one fatty substance,
at least one surfactant, and
at least one alkaline agent.

Process

The present invention also relates to a process for dyeing keratin fibers, preferably the hair, which comprises the step of applying to said keratin fibers an effective amount of a composition as defined previously.

The composition may be applied to wet or dry keratin fibers. On conclusion of the treatment, the keratin fibers are optionally rinsed with water, optionally washed with a shampoo and then rinsed with water, before being dried or left to dry.

Preferably, the process according to the invention comprises a step of mixing the composition according to the invention with an oxidizing composition comprising at least one chemical oxidizing agent. This mixing step is preferably performed at the time of use, just before applying to the hair the composition resulting from the mixing.

More particularly, the chemical oxidizing agent(s) are chosen from hydrogen peroxide, urea peroxide, alkali metal bromates or ferricyanides, peroxygenated salts, for instance persulfates, perborates, peracids and precursors thereof and percarbonates of alkali metals or alkaline-earth metals, and mixtures thereof. The chemical oxidizing agent is preferably hydrogen peroxide.

The oxidizing composition is preferably an aqueous composition. In particular, it comprises more than 5% by weight of water, preferably more than 10% by weight of water and even more advantageously more than 20% by weight of water.

It may also comprise one or more organic solvents chosen from those listed previously; these solvents more particularly representing, when they are present, from 1% to 40% by weight and preferably from 5% to 30% by weight, relative to the weight of the oxidizing composition.

The oxidizing composition also preferably comprises one or more acidifying agents. Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

The oxidizing composition may also comprise fatty substances such as those described previously, preferably chosen from fatty alcohols, liquid hydrocarbons comprising more than 16 carbon atoms and mixtures thereof, surfactants and polymers.

Usually, the pH of the oxidizing composition, when it is aqueous, is less than 7, preferably between 1 and 5, preferentially between 1.5 and 4.5.

Preferably, the oxidizing composition comprises hydrogen peroxide as oxidizing agent, in aqueous solution, the concentration of which ranges, more particularly, from 0.1% to 50%, more particularly between 0.5% and 20% and even more preferentially between 1% and 15% by weight, relative to the weight of the oxidizing composition.

Preferably, at least one of the compositions (dye composition or oxidizing composition) is aqueous.

Preferably, the process according to the invention comprises a step of applying to the hair a composition resulting from the mixing, at the time of use, of at least two compositions:

a) a dye composition comprising:

at least one oxidation base chosen from the derivatives of para-phenylenediamine of formula (I), addition salts thereof, solvates thereof and/or solvates of the salts thereof:

(I)

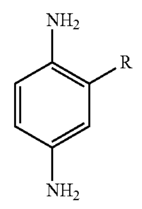

in which R is chosen from:
i) a $(C_1-C_4)$alkoxy$(C_1-C_4)$alkyl radical,
ii) a $C_1-C_4$ hydroxyalkyl radical;

at least one oxidation coupler chosen from 6-hydroxybenzomorpholine of formula (II), an addition salt thereof, solvates thereof and/or solvates of the salts thereof and mixtures thereof:

(II)

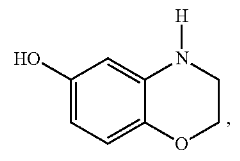

at least one (poly)oxyalkylenated amino silicone, and optionally at least one alkaline agent; and b) an oxidizing composition comprising one or more chemical oxidizing agents, preferably hydrogen peroxide.

According to a particular embodiment, the process according to the invention comprises the step of applying to the hair a composition resulting from the mixing, at the time of use, of at least two compositions:

a) a dye composition comprising:

at least one oxidation base chosen from the derivatives of para-phenylenediamine of formula (I), addition salts thereof, solvates thereof and/or solvates of the salts thereof:

(I)

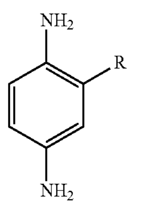

in which R is chosen from:

i) a ($C_1$-$C_4$)alkoxy($C_1$-$C_4$)alkyl radical, ii) a $C_1$-$C_4$ hydroxyalkyl radical;

at least one oxidation coupler chosen from 6-hydroxybenzomorpholine of formula (II), an addition salt thereof, solvates thereof and/or solvates of the salts thereof and mixtures thereof:

(II)

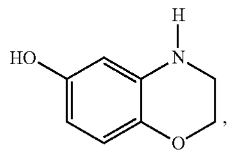

at least one (poly)oxyalkylenated amino silicone;

at least one fatty substance, at least one, preferably anionic, surfactant, and at least one alkaline agent; and b) an oxidizing composition comprising one or more chemical oxidizing agents, preferably hydrogen peroxide.

The invention also relates to a composition comprising:

at least one oxidation base chosen from the derivatives of para-phenylenediamine of formula (I), addition salts thereof, solvates thereof and/or solvates of the salts thereof:

(I)

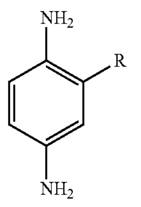

in which R is chosen from:

i) a ($C_1$-$C_4$)alkoxy($C_1$-$C_4$)alkyl radical, ii) a $C_1$-$C_4$ hydroxyalkyl radical;

at least one oxidation coupler chosen from 6-hydroxybenzomorpholine of formula (II), an addition salt thereof, solvates thereof and/or solvates of the salts thereof and mixtures thereof:

(II)

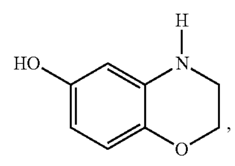

at least one (poly)oxyalkylenated amino silicone, and one or more chemical oxidizing agents, preferably hydrogen peroxide, this composition being a ready-to-use composition.

This ready-to-use composition may comprise one or more ingredients among those described above.

Preferably, the pH of the ready-to-use composition is between 8 and 11, preferentially between 9 and 10.5.

Kit Another subject of the invention is a multi-compartment device for dyeing keratin fibers, comprising at least a first compartment containing the dye composition according to the invention and at least a second compartment containing an oxidizing composition as described above.

The compositions of the device according to the invention are packaged in separate compartments, optionally accompanied by suitable application means, which may be identical or different, such as fine brushes, coarse brushes or sponges.

The device mentioned above may also be equipped with a means for dispensing the desired mixture onto the hair, for instance the devices described in patent FR 2 586 913.

Finally, the present invention relates to the use of a composition as described above, for dyeing keratin fibers, and in particular the hair.

The examples that follow serve to illustrate the invention without, however, being limiting in nature.

EXAMPLES

In the examples that follow, all the amounts are given as mass percentages of active material (AM) relative to the total weight of the composition (unless otherwise mentioned).

Example 1

Dye Composition

Composition A1 according to the present invention and comparative composition C1 were prepared using the ingredients whose contents are indicated in the table below (g %):

TABLE 1

| | A1 (Invention) | C1 (comparative) |
|---|---|---|
| 2-METHOXYMETHYL-P-PHENYLENEDIAMINE | 0.96 | 0.96 |
| N,N-BIS(2-HYDROXYETHYL)-p-PHENYLENEDIAMINE SULFATE | 0.2 | 0.2 |
| HYDROXYBENZOMORPHOLINE | 0.3 | 0.3 |
| m-AMINOPHENOL | 0.31 | 0.31 |
| 2,4-DIAMINOPHENOXYETHANOL HCL | 0.043 | 0.043 |
| HYDROXYETHYL-3,4-METHYLENEDIOXYANILINE HCL | 0.43 | 0.43 |
| PEG-40/PPG-8 METHYLAMINOPROPYL/HYDROXYPROPYL DIMETHICONE COPOLYMER | 0.33 | — |
| AMODIMETHICONE | — | 0.33 |
| ISOPROPYL MYRISTATE | 0.6 | 0.6 |
| MYRISTIC ACID | 0.12 | 0.12 |
| PALMITIC ACID | 1.76 | 1.76 |
| STEARIC ACID | 2.12 | 2.12 |
| CETEARYL ALCOHOL | 13.5 | 13.5 |
| CETRIMONIUM CHLORIDE | 0.145 | 0.145 |
| COCAMIDE MEA | 2.5 | 2.5 |
| CETEARETH-25 | 4 | 4 |
| SODIUM LAURYL SULFATE | 0.275 | 0.275 |
| POLYQUATERNIUM-6 | 0.4 | 0.4 |
| DIPROPYLENE GLYCOL | 0.121 | 0.121 |
| GLYCERIN | 0.374 | 0.374 |
| PROPYLENE GLYCOL | 1 | 1 |
| TETRASODIUM EDTA | 0.051 | 0.051 |
| AMMONIUM HYDROXIDE | 2.06 | 2.06 |
| ASCORBIC ACID | 0.4 | 0.4 |
| SODIUM HYDROXIDE | 0.3 | 0.3 |
| SODIUM SULFITE | 0.8 | 0.8 |
| water | qs 100 | qs 100 |

Oxidizing Composition

The oxidizing composition B1 was prepared from the ingredients whose contents are indicated in the table below:

TABLE 2

| | B1 |
|---|---|
| HYDROGEN PEROXIDE | 5.5 |
| CETEARYL ALCOHOL | 2.4 |
| SODIUM LAURYL SULFATE | 0.316 |
| TETRASODIUM EDTA | 0.204 |
| SODIUM BENZOATE | 0.3 |
| ETIDRONIC ACID | 0.09 |
| CITRIC ACID | 0.3 |
| Water | qs 100 |

Dyeing Protocol

The dye compositions A1 and C1 are each respectively mixed with the oxidizing composition B1 in a 1+1.5 weight ratio.

Each of the mixtures is applied to locks of hair which contain 90% natural white hairs (NW) on the one hand and are permanent-waved (PW) on the other hand, at a rate of 5 g of mixture per 1 g of hair.

After a leave-on time of 30 minutes on a hotplate at 27° C., the hair is rinsed, washed with a standard shampoo and then dried.

Results

The coloring of the hair is evaluated in the L*a*b* system, using a Konica Minolta CM-3600A spectrocolorimeter (illuminant D65, angle 10°, specular component included) in the CIELab system.

In this system, L* represents the lightness. The lower the value of L*, the darker and more powerful the coloring obtained. The chromaticity is measured by the values a* and b*, a* representing the red/green axis and b* the yellow/blue axis.

The selectivity is represented by the color difference ΔE between the locks of dyed natural hair (NW) and dyed permanent-waved hair (PW), ΔE being obtained from the formula:

$$\Delta E = \sqrt{(L^* - L_0^*)^2 + (a^* - a_0^*)^2 + (b^* - b_0^*)^2}$$

in which L* represents the intensity and a* and b* represent the chromaticity of the dyed natural hair and $L_0$* represents the intensity and $a_0$* and $b_0$* represent the chromaticity of the dyed permanent-waved hair. The lower the value of ΔE, the lower the selectivity and the more uniform the coloration along the hair.

TABLE 3

| Composition | Type of hair | L* | a* | b* | ΔE |
|---|---|---|---|---|---|
| A1 (invention) | NW | 20.13 | 0.39 | 3.06 | 2.30 |
| | PW | 18.20 | −0.09 | 1.90 | |
| B1 (comparative) | NW | 24.63 | 0.04 | 3.56 | 6.70 |
| | PW | 18.42 | 0.13 | 1.05 | |

Composition according to the invention A1 leads to a lower ΔE value, and thus to better selectivity, relative to the comparative composition C1.

Example 2

Dye Compositions

Composition A2 according to the present invention and comparative composition C2 were prepared using the ingredients whose contents are indicated in the table below:

TABLE 4

| | A2 (Invention) | C2 (comparative) |
|---|---|---|
| HYDROXYETHYL-p-PHENYLENEDIAMINE SULFATE | 1.59 | 1.59 |
| N,N-BIS(2-HYDROXYETHYL)-p-PHENYLENEDIAMINE SULFATE | 0.2 | 0.2 |
| HYDROXYBENZOMORPHOLINE | 0.3 | 0.3 |
| m-AMINOPHENOL | 0.31 | 0.31 |
| 2,4-DIAMINOPHENOXYETHANOL HCL | 0.043 | 0.043 |
| HYDROXYETHYL-3,4-METHYLENEDIOXYANILINE HCL | 0.43 | 0.43 |
| PEG-40/PPG-8 METHYLAMINOPROPYL/HYDROXYPROPYL DIMETHICONE COPOLYMER | 0.33 | — |
| AMODIMETHICONE | — | 0.33 |
| ISOPROPYL MYRISTATE | 0.6 | 0.6 |
| MYRISTIC ACID | 0.12 | 0.12 |
| PALMITIC ACID | 1.76 | 1.76 |
| STEARIC ACID | 2.12 | 2.12 |
| CETEARYL ALCOHOL | 13.5 | 13.5 |
| CETRIMONIUM CHLORIDE | 0.145 | 0.145 |
| COCAMIDE MEA | 2.5 | 2.5 |
| CETEARETH-25 | 4 | 4 |
| SODIUM LAURYL SULFATE | 0.275 | 0.275 |
| POLYQUATERNIUM-6 | 0.4 | 0.4 |
| DIPROPYLENE GLYCOL | 0.121 | 0.121 |
| GLYCERIN | 0.374 | 0.374 |
| PROPYLENE GLYCOL | 1 | 1 |
| TETRASODIUM EDTA | 0.051 | 0.051 |
| AMMONIUM HYDROXIDE | 2.06 | 2.06 |
| ASCORBIC ACID | 0.4 | 0.4 |
| SODIUM HYDROXIDE | 0.3 | 0.3 |
| SODIUM SULFITE | 0.8 | 0.8 |
| water | qs 100 | qs 100 |

Dyeing Protocol

The dye compositions A2 and C2 are each respectively mixed with the oxidizing composition B1 in a 1+1.5 weight ratio.

Each of the mixtures is applied to locks of hair which contain 90% natural white hairs (NW) on the one hand and are permanent-waved (PW) on the other hand, at a rate of 5 g of mixture per 1 g of hair.

After a leave-on time of 30 minutes on a hotplate at 27° C., the hair is rinsed, washed with a standard shampoo and then dried.

Results

The coloring of the hair is evaluated as in example 1 in the L*a*b* system, using a Konica Minolta CM-3600A spectrocolorimeter (illuminant D65, angle 10°, specular component included) in the CIELab system.

TABLE 6

| Composition | Type of hair | L* | a* | b* | ΔE |
|---|---|---|---|---|---|
| A2 + B1 | NW | 20.56 | −0.22 | 3.03 | 3.66 |
| (invention) | PW | 18.69 | −0.06 | −0.11 | |
| C2 + B1 | NW | 21.60 | −0.42 | 3.79 | 6.01 |
| (comparative) | PW | 16.33 | 0.14 | 0.96 | |

Composition according to the invention A2 leads to a lower ΔE value, and thus to better selectivity, relative to the comparative composition C2.

The invention claimed is:

1. A composition comprising:

at least one oxidation base chosen from derivatives of para-phenylenediamine of formula (I), addition salts thereof, solvates thereof, or solvates of the salts thereof:

(I)

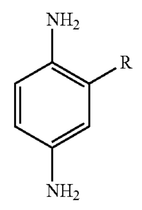

wherein R is chosen from:

i) a ($C_1$-$C_4$) alkoxy ($C_1$-$C_4$) alkyl radical, ii) a $C_1$-$C_4$ hydroxyalkyl radical;

at least one oxidation coupler chosen from 6-hydroxybenzomorpholine of formula (II), addition salts thereof, solvates thereof, solvates of the salts thereof or mixtures thereof:

(II)

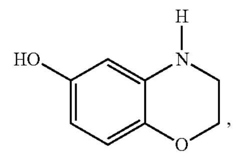

and at least one (poly)oxyalkylenated amino silicone chosen from (poly)oxyalkylenated amino silicones having the INCI name PEG-40/PPG-8 methylaminopropyl/hydroxypropyl dimethicone copolymer.

2. The composition according to claim 1, wherein the at least one oxidation base of formula (I) is chosen from 2-methoxymethyl-para-phenylenediamine, 2-β-hydroxypropyl-para-phenylenediamine, 2-γ-hydroxyethyl-para-phenylenediamine, addition salts thereof, solvates thereof, or solvates of the salts thereof.

3. The composition according to claim 1, wherein the total content of oxidation base(s) chosen from derivatives of para-phenylenediamine of formula (I), addition salts thereof, solvates thereof, or solvates of the salts thereof ranges from 0.001% to 20% by weight, relative to the total weight of the composition.

4. The composition according to claim 1, wherein the total content of oxidation coupler(s) chosen from 6-hydroxybenzomorpholine of formula (II), addition salts thereof, solvates thereof, or solvates of the salts thereof ranges from 0.001% to 20% by weight, relative to the total weight of the composition.

5. The composition according to claim 1, wherein the weight ratio between the total content of the oxidation base(s) chosen from the derivatives of para-phenylenediamine of formula (I), addition salts thereof, solvates thereof, or solvates of the salts thereof and the total content of oxidation coupler(s) chosen from 6-hydroxybenzomorpholine of formula (II), addition salts thereof, solvates thereof, or solvates of the salts thereof ranges from 0.1 to 10.

6. The composition according to claim 1, in which the (poly)oxyalkylenated amino silicone(s) are chosen from (AB) n type multiblock (poly)oxyalkylenated amino silicones, A being a polysiloxane block and B being a (poly) oxyalkylene block, comprising at least one amine group, wherein said (poly)oxyalkylenated amino silicones are formed from repeating units having the following general formulae (x) or (xx):

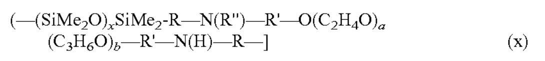

$$(\text{—}(SiMe_2O)_xSiMe_2\text{-}R\text{—}N(R'')\text{—}R'\text{—}O(C_2H_4O)_a(C_3H_6O)_b\text{—}R'\text{—}N(H)\text{—}R\text{—}] \quad (x)$$

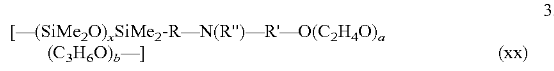

$$[\text{—}(SiMe_2O)_xSiMe_2\text{-}R\text{—}N(R'')\text{—}R'\text{—}O(C_2H_4O)_a(C_3H_6O)_b\text{—}] \quad (xx)$$

wherein, in (x) and (xx):

a is an integer greater than or equal to 1;

b is an integer between 0 and 200;

x is an integer ranging from 1 to 10 000, more particularly from 10 to 5000;

R" is a hydrogen atom or a methyl;

R, which may be identical or different, represents a linear or branched divalent $C_2$-$C_{12}$ hydrocarbon-based radical optionally including one or more heteroatoms; and R', which may be identical or different, represents a linear or branched divalent $C_2$-$C_{12}$ hydrocarbon-based radical optionally including one or more heteroatoms.

7. The composition according to claim 1, wherein the (poly)oxyalkylenated amino silicone(s) is (are) present in a total content ranging from 0.01% to 10% by weight, relative to the total weight of the composition.

8. The composition according to claim 1, further comprising at least one fatty substance other than (poly)oxyalkylenated amino silicones, wherein the at least one fatty substance is from chosen from liquid fatty substances, solid fatty substances and mixtures thereof.

9. The composition according to claim 1, wherein the at least one liquid fatty substance other than (poly)oxyalkylenated amino silicones is chosen from liquid hydrocarbons containing more than 16 carbon atoms, plant oils, liquid fatty alcohols, liquid fatty esters and mixtures thereof.

10. The composition according to claim 1, wherein the at least one solid fatty substance is chosen from solid fatty acids, solid fatty alcohols, solid esters of fatty acids, solid esters of fatty alcohols, waxes, ceramides, or mixtures thereof.

11. The composition according to claim 1, further comprising at least one surfactant.

12. The composition according to claim 1, further comprising at least one cationic polymer.

13. The composition according to claim 1, further comprising at least one alkaline agent.

14. The composition according to claim 1, wherein the composition does not comprise any chemical oxidizing agent.

15. The composition according to claim 1, further comprising at least one chemical oxidizing agent.

16. A process for dyeing keratin fibers, comprising applying to said keratin fibers the composition according to claim 15.

17. The process for dyeing keratin fibers according to claim 16, wherein the composition is prepared by mixing, at least a) a dyeing composition and b) an oxidizing composition, wherein:

a) the dyeing composition comprises:

at least one oxidation base chosen from the derivatives of para-phenylenediamine of formula (I), addition salts thereof, solvates thereof, or solvates of the salts thereof:

(I)

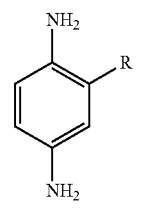

wherein R is chosen from:

i) a ($C_1$-$C_4$) alkoxy ($C_1$-$C_4$) alkyl radical, ii) a $C_1$-$C_4$ hydroxyalkyl radical;

at least one oxidation coupler chosen from 6-hydroxybenzomorpholine of formula (II), addition salts thereof, solvates thereof, solvates of the salts thereof or mixtures thereof:

(II)

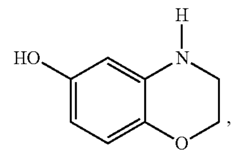

and at least one (poly)oxyalkylenated amino silicone chosen from (poly)oxyalkylenated amino silicones having the INCI name PEG-40/PPG-8 methylaminopropyl/hydroxypropyl dimethicone copolymer; and b) an oxidizing composition comprising one or more chemical oxidizing agents.

18. A multi-compartment device, comprising a first compartment comprising a) a dyeing composition and b) a second compartment comprising an oxidizing composition, wherein:

a) the dyeing composition comprises:

at least one oxidation base chosen from the derivatives of para-phenylenediamine of formula (I), addition salts thereof, solvates thereof, or solvates of the salts thereof:

(I)

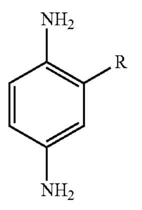

wherein R is chosen from:

i) a $(C_1-C_4)$ alkoxy $(C_1-C_4)$ alkyl radical, ii) a $C_1-C_4$ hydroxyalkyl radical;

at least one oxidation coupler chosen from 6-hydroxybenzomorpholine of formula (II), addition salts thereof, solvates thereof, solvates of the salts thereof, or mixtures thereof:

(II)

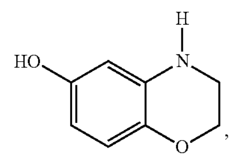

, and at least one (poly)oxyalkylenated amino silicone chosen from (poly)oxyalkylenated amino silicones having the INCI name PEG-40/PPG-8 methylaminopropyl/hydroxypropyl dimethicone copolymer; and b) an oxidizing composition comprising one or more chemical oxidizing agents.

* * * * *